(12) United States Patent
Mello et al.

(10) Patent No.: US 6,620,917 B1
(45) Date of Patent: Sep. 16, 2003

(54) METHOD FOR THE PURIFICATION AND AQUEOUS FIBER SPINNING OF SPIDER SILKS AND OTHER STRUCTURAL PROTEINS

(75) Inventors: Charlene Mello, Rochester, MA (US); Steven Arcidiacono, Bellingham, MA (US); Michelle M. Butler, Auburn, MA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/490,291

(22) Filed: Jan. 20, 2000

(51) Int. Cl.$^7$ .......................... C07K 1/00; C07K 14/00; C12P 21/00
(52) U.S. Cl. ...................... 530/412; 530/353; 530/350; 530/422; 530/425; 435/69.1
(58) Field of Search ................................ 536/353, 350, 536/412, 422, 425; 435/69.1

(56) References Cited

U.S. PATENT DOCUMENTS

| | | | |
|---|---|---|---|
| 5,156,956 A | 10/1992 | Motoki et al. | 435/68.1 |
| 5,243,038 A | 9/1993 | Ferrari et al. | 536/23.1 |
| 5,245,012 A | 9/1993 | Lombari et al. | 530/353 |
| 5,514,581 A | 5/1996 | Ferrari et al. | 435/252.3 |
| 5,641,648 A | 6/1997 | Ferrari et al. | 435/69.1 |
| 5,728,810 A | 3/1998 | Lewis et al. | 530/353 |

*Primary Examiner*—Christopher S. F. Low
*Assistant Examiner*—Holly Schnizer
(74) *Attorney, Agent, or Firm*—Vincent J. Ranucci

(57) ABSTRACT

Methods are described for the purification and spinning of recombinant and non-recombinant proteins. Specifically, the lysis of bacteria and purification of silk proteins occur in a single solution of organic acid. Bacterial proteins are hydrolyzed while the silk protein remains intact. Silk proteins remain soluble as they are concentrated into a aqueous-based mixture for fiber spinning.

14 Claims, 12 Drawing Sheets

(2 of 12 Drawing Sheet(s) Filed in Color)

```
ATGAGAGGATCGCATCACCATCACCATCACGGATCCATGGCTAGCGGTAGAGGCGGGCTGGGTGGCCAG
GGTGCAGGTGCGGCTGCGGCTGCCGCGGCAGCGGCCGCAGGCGGTGCCGGCCAAGGTGGCTATGGCGGC
CTGGGTTCTCAGGGGACTAGCGGTAGAGGCGGGCTGGGTGGCCAGGGTGCAGGTGCGGCTGCGGCTGCC
GCGGCAGCGGCCGCAGGCGGTGCCGGCCAAGGTGGCTATGGCGGCCTGGGTTCTCAGGGGACTAGCGGT
AFAGGCGGGCTGGGTGGCCAGGGTGCAGGTGCGGCTGCGGCTCCCGCGGCAGCGGCCGCAGGCGGTGC
CGGCCAAGGTGGCTATGGCGGCCTGGGTTCTCAGGGGACTAGCGGTAGAGGCGGGCTGGGTGGCCAGGG
TGCAGGTGCGGCTGCGGCTGCCGCGGCAGCGGCCGCAGGCGGTGCCGGCCAAGGTGGCTATGGCGGCCT
GGGTTCTCAGGGGACTAGCGGTAGAGGCGGGCTGGGTGGCCAGGGTGCAGGTGCGGCTGCGGCTGCCGC
GGCAGCGGCCGCAGGCGGTGCCGGCCAAGGTGGCTATGGCGGCCTGGGTTCTCAGGGGACTAGCGGTAG
AGGCGGGCTGGGTGGCCAGGGTGCAGGTGCGGCTGCGGCTGCCGCGGCAGCGGCCGCAGG
CGGTGCCGGCCAAGGYGGCTATGGCGGCCTGGGTTCTCAGGGGACTAGCGGTAGAGGCGGGCTGGGTGG
CCAGGGTGCAGGTGCGGCTGCGGCTGCCGCGGCAGCGGCCGCAGGCGGTGCCGGCCAAGGTGGCTATGG
CGGCCTGGGTTCTCAGGGGACTAGTGGGATCCGTCGACCTGCAGCCAAGCTTAATTAG
```

FIG. 1

```
MRGSHHHHHHGSMASGRGGLGGQGAGAAAAAAAAAAAGGAGQGGYGGLGSQGTSGRGGLGGQGAGAAA
AAAAAAAGGAGQGGYGGLGSQGTSGRGGLGGQGAGAAAAAAAAAAAGGAGQGGYGGLGSQGTSGRGGLG
GQGAGAAAAAAAAAAAGGAGQGGYGGLGSQGTSGRGGLGGQGAGAAAAAAAAAAAGGAGQGGYGGLGSQ
GTSGRGGLGGQGAGAAAAAAAAAAAGGAGQGGYGGLGSQGTSGRGGLGGQGAGAAAAAAAAAAAGGAGQ
GGYGGLGSQGTSGIRRPAAKLN
```

FIG. 2

```
ATGAGAGGATCGCATCACCATCACCCATCACGGATCCATGGCTAGCGGTAGAGGCGGGCTGGGTGGCCAG
GGTGCAGGTGCGGCTGCGGCTGCCGCGGCAGCGGGCCGCAGGCGGTGCCGGCCAAGGTGGCTATGGCGGC
CTGGGTTCTCAGGGGACTAGCGGTAGAGGCGGGCTGGGTGGCCAGGGTGCAGGTGCGGCTGCGGCTGCC
GCGGCAGCGGCCGCAGGCGGTGCCGGCCAAGGTGGCTATGGCGGCCTGGGTTCTCAGGGGACTAGCGGT
AGAGGCGGGCTGGGTGGCCAGGGTGCAGGTGCGGCTGCGGCTGCCGCGGCAGCGGCCGCAGGCGGTGC
CGGCCAAGGTGGCTATGGCGGCCTGGGTTCTCAGGGGACTAGCGGTAGAGGCGGGCTGGGTGGCCAGGG
TGCAGGTGCGGCTGCGGCTGCCGCGGCAGCGGCCGCAGGCGGTGCCGGCCAAGGTGGCTATGGCGGCCT
GGGTTCTCAGGGGACTAGCGGTCCGGGCGGTTATGGTCCGGGTCAACAAACTAGCGGTAGAGGCGGGCT
GGGTGGCCAGGGTGCAGGTGCGGCTGCGGCTGCCGCGGCAGCGGCCGCAGGCGGTGCCGGCCAAGGTG
GCTATGGCGGCCTGGGTTCTCAGGGGACTAGCGGTAGAGGCGGGCTGGGTGGCCAGGGTGCAGGTGCGG
CTGCGGCTGCCGCGGCAGCGGCCGCAGGCGGTGCCGGCCAAGGTGGCTATGGCGGCCTGGGTTCTCAGG
GGACTAGCGGTAGAGGCGGGCTGGGTGGCCAGGGTGCAGGTGCGGCTGCGGCTGCCGCGGCAGCGGCC
GCAGGCGGTGCCGGCCAAGGTGGCTATGGCGGCCTGGGTTCTCAGGGGACTAGCGGTAGAGGCGGGCTG
GGTGGCCAGGGTGCAGGTGCGGCTGCGGCTGCCGCGGCAGCGGCCGCAGGCGGTGCCGGCCAAGGTGG
CTATGGCGGCCTGGGTTCTCAGGGGACTAGCGGTCCGGGCGGTTATGGTCCGGGTCAACAAACTAGCGG
TAGAGGCGGGCTGGGTGGCCAGGGTGCAGGTGCGGCTGCGGCTGCCGCGGCAGCGGCCGCAGGCGGTG
CCGGCCAAGGTGGCTATGGCGGCCTGGGTTCTCAGGGGACTAGCGGTAGAGGCGGGCTGGGTGGCCAGG
GTGCAGGTGCGGCTGCGGCTGCCGCGGCAGCGGCCGCAGGCGGTGCCGGCCAAGGTGGCTATGGCGGCC
TGGGTTCTCAGGGGACTAGCGGTAGAGGCGGGCTGGGTGGCCAGGGTGCAGGTGCGGCTGCGGCTGCCG
CGGCAGCGGCCGCAGGCGGTGCCGGCCAAGGTGGCTATGGCGGCCTGGGTTCTCAGGGGACTAGCGGTA
GAGGCGGGCTGGGTGGCCAGGGTGCAGGTGCGGCTGCGGCTGCCGCGGCAGCGGCCGCAGGCGGTGCC
GGCCAAGGTGGCTATGGCGGCCTGGGTTCTCAGGGGACTAGCGGTCCGGGCGGTTATGGTCCGGGTCAA
CAAACTAGCGGTAGAGGCGGGCTGGGTGGCCAGGGTGCAGGTGCGGCTGCGGCTGCCGCGGCAGCGGC
CGCAGGCGGTGCCGGCCAAGGTGGCTATGGCGGCCTGGGTTCTCAGGGGACTAGCGGTAGAGGCGGGCT
GGGTGGCCAGGGTGCAGGTGCGGCTGCGGCTGCCGCGGCAGCGGCCGCAGGCGGTGCCGGCCAAGGTG
GCTATGGCGGCCTGGGTTCTCAGGGGACTAGCGGTAGAGGCGGGCTGGGTGGCCAGGGTGCAGGTGCGG
CTGCGGCTGCCGCGGCAGCGGCCGCAGGCGGTGCCGGCCAAGGTGGCTATGGCGGCCTGGGTTCTCAGG
GGACTAGCGGTAGAGGCGGGCTGGGTGGCCAGGGTGCAGGTGCGGCTGCGGCTGCCGCGGCAGCGGCC
GCAGGCGGTGCCGGCCAAGGTGGCTATGGCGGCCTGGGTTCTCAGGGGACTAGCGGTCCGGGCGGTTAT
GGTCCGGGTCAACAAACTAGTGGGATCCGTCGACCTGCAGCCAAGCTTAATTAG
```

FIG. 3

```
MRGSHHHHHHGSMASGRGGLGGQGAGAAAAAAAAAGGAGQGGYGGLGSQGTSGRGGLGGQGAGAA
AAAAAAAAGGAGQGGYGGLGSQGTSGRGGLGGQGAGAAAAAAAAAGGAGQGGYGGLGSQGTSGRG
GLGGQGAGAAAAAAAAAGGAGQGCYGGLGSQGTSGPGGYGPGQQTSGRGGLGGQGAGAAAAAAAA
AGGAGQGGYGGLGSQGTSGRGGLGGQGAGAAAAAAAAAGGAGQGGYGGLGSQGTSGRGGLGGQGAG
AAAAAAAAAGGAGQGGYGGLGSQGTSGRGGLGGQGAGAAAAAAAAAGGAGQGGYGGLGSQGTSGP
GGYGPGQQTSGRGGLGGQGAGAAAAAAAAAGGAGQGGYGGLGSQGTSGRGGLGGQGAGAAAAAA
AAAGGAGQGGYGGLGSQGTSGRGGLGGQGAGAAAAAAAAAGGAGQGGYGGLGSQGTSGRGGLGGQG
AGAAAAAAAAAGGAGQGGYGGLGSQGTSGPGGYGPGQQTSGRGGLGGQGAGAAAAAAAAAGGAG
QGGYGGLGSQGTSGRGGLGGQGAGAAAAAAAAAGGAGQGGYGGLGSQGTSGRGGLGGQGAGAAAA
AAAAGGAGQGGYGGLGSQGTSGRGGLGGQGAGAAAAAAAAAGGAGQGGYGGLGSQGTSGPGGYGP
GQQTSGIRRPAAKLN
```

FIG. 4

```
ATGGCTAGCATGACTGGTGGACAGCAAATGGGTCGCGGATCCATGGCTAGCGGTAGAGGCGGGCTGGGT
GGCCAGGGTGCAGGTGCGGCTGCGGCTGCCGCGGCAGCGGCCGCAGGCGGTGCCGGCCAAGGTGGCTAT
GGCGGCCTGGGTTCTCAGGGGACTAGCGGTAGAGGCGGGCTGGGTGGCCAGGGTGCAGGTGCGGCTGCG
GCTGCCGCGGCAGCGGCCGCAGGCGGTGCCGGCCAAGGTGGCTATGGCGGCCTGGGTTCTCAGGGGACT
AGCGGTAGAGGCGGGCTGGGTGGCCAGGGTGCAGGTGCGGCTGCGGCTGCCGCGGCAGCGGCCGCAGG
CGGTGCCGGCCAAGGTGGCTATGGCGGCCTGGGTTCTCAGGGGACTAGCGGTAGAGGCGGGCTGGGTGG
CCAGGGTGCAGGTGCGGCTGCGGCTGCCGCGGCAGCGGCCGCAGGCGGTGCCGGCCAAGGTGGCTATGG
CGGCCTGGGTTCTCAGGGGACTAGCGGTCCGGCGGTTATGGTCCGGGTCAACAAACTAGCGGTAGAGG
CGGGCTGGGTGGCCAGGGTGCAGGTGCGGCTGCGGCTGCCGCGGCAGCGGCCGCAGGCGGTGCCGGCCA
AGGTGGCTATGGCGGCCTGGGTTCTCAGGGGACTAGCGGTAGAGGCGGGCTGGGTGGCCAGGGTGCAGG
TGCGGCTGCGGCTGCCGCGGCAGCGGCCGCAGGCGGTGCCGGCCAAGGTGGCTATGGCGGCCTGGGTTC
TCAGGGGACTAGCGGTAGAGGCGGGCTGGCTGGCCAGGGTGCAGGTGCGGCTGCGGCTGCCGCGGCAG
CGGCCGCAGGCGGTGCCGGCCAAGGTGGCTATGGCGGCCTGGGTTCTCAGGGGACTAGCGGTAGAGGCG
GGCTGGGTGGCCAGGGTGCAGGTGCGGCTGCGGCTGCCGCGGCAGCGGCCGCAGGCGGTGCCGGCCAA
GGTGGCTATGGCGGCCTGGGTTCTCAGGGGACTAGCGGTCCGGCGGTTATGGTCCGGGTCAACAAACT
AGCGGTAGAGGCGGGCTGGGTGGCCAGGGTGCAGGTGCGGCTGCGGCTGCCGCGGCAGCGGCCGCAGG
CGGTGCCGGCCAAGGTGGCTATGGCGGCCTGGGTTCTCAGGGGACTAGCGGTAGAGGCGGGCTGGGTGG
CCAGGGTGCAGGTGCGGCTGCGGCTGCCGCGGCAGCGGCCGCAGGCGGTGCCGGCCAAGGTGGCTATGG
CGGCCTGGGTTCTCAGGGGACTAGCGGTAGAGGCGGGCTGGGTGGCCAGGGTGCAGGTGCGGCTGCGGC
TGCCGCGGCAGCGGCCGCAGGCGGTGCCGGCCAAGGTGGCTATGGCGGCCTGGGTTCTCAGGGGACTAG
CGGTAGAGGCGGGCTGGGTGGCCAGGGTGCAGGTGCGGCTGCGGCTGCCGCGGCAGCGGCCGCAGGCG
GTGCCGGCCAAGGTGGCTATGGCGGCCTGGGTTCTCAGGGGACTAGCGGTCCGGCGGTTATGGTCCGG
GTCAACAAACTAGCGGTAGAGGCGGGCTGGGTGGCCAGGGTGCAGGTGCGGCTGCGGCTGCCGCGGCA
GCGGCCGCAGGCGGTGCCGGCCAAGGTGGCTATGGCGGCCTGGGTTCTCAGGGGACTAGCGGTAGAGGC
GGGCTGGGTGGCCAGGGTGCAGGTGCGGCTGCGGCTGCCGCGGCAGCGGCCGCAGGCGGTGCCGGCCA
AGGTGGCTATGGCGGCCTGGGTTCTCAGGGGACTAGCGGTAGAGGCGGGCTGGGTGGCCAGGGTGCAGG
TGCGGCTGCGGCTGCCGCGGCAGCGGCCGCAGGCGGTGCCGGCCAAGGTGGCTATGGCGGCCTGGGTTC
TCAGGGGACTAGCGGTAGAGGCGGGCTGGGTGGCCAGGGTGCAGGTGCGGCTGCGGCTGCCGCGGCAG
CGGCCGCAGGCGGTGCCGGCCAAGGTGGCTATGGCGGCCTGGGTTCTCAGGGGACTAGCGGTCCGGGCG
GTTATGGTCCGGGTCAACAAACTAGTGGGATCCGAATTCGAGCTCCGTCGACAAGCTTCGAGCACCACC
ACCACCACTGA
```

FIG. 5

MASMTGGQQMGRGSMASGRGGLGGQGAGAAAAAAAAAAGGAGQGGYGGLGSQGTSGRGGLGGQGAGA
AAAAAAAAGGAGQGGYGGLGSQGTSGRGGLGGQGAGAAAAAAAAAAGGAGQGGYGGLGSQGTSGRG
GLGGQGAGAAAAAAAAAAGGAGQGGYGGLGSQGTSGPGGYGPGQQTSGRGGLGGQGAGAAAAAAAA
GGAGQGGYGGLGSQGTSGRGGLGGQGAGAAAAAAAAAAGGAGQGGYGGLGSQGTSGRGGLGGQGAGAA
AAAAAAAAGGAGQGGYGGLGSQGTSGRGGLGGQGAGAAAAAAAAAAGGAGQGGYGGLGSQGTSGPGGY
GPGQQTSGRGGLGGQGAGAAAAAAAAAAGGAGQGGYGGLGSQGTSGRGGLGGQGAGAAAAAAAAAAG
GAGQGGYGGLGSQGTSGRGGLGGQGAGAAAAAAAAAAGGAGQGGYGGLGSQGTSGRGGLGGQGAGAAA
AAAAAAGGAGQGGYGGLGSQGTSGPGGYGPGQQTSGRGGLGGQGAGAAAAAAAAAAGGAGQGGYGGL
GSQGTSGRGGLGGQGAGAAAAAAAAAAGGAGQGGYGGLGSQGTSGRGGLGGQGAGAAAAAAAAAAGG
AGQGGYGGLGSQGTSGRGGLGGQGAGAAAAAAAAAAGGAGQGGYGGLGSQGTSGPGGYGPGQQTSGIRIR
APSTSFEHHHHHH

FIG. 6

ATGGCTAGCATGACTGGTGGACAGCAAATGGGTCGGATCCGAATTCGTGGATATGGAGGTCTTGGTGGA
CAAGGTGCCGGACAAGGAGCTGGTGCAGCCGCCGCAGCAGCAGCTGGTGGTGCCGGACAAGGAGGATA
TGGAGGTCTTGGAAGCCAAGGTGCTGGACGAGGTGGACAAGGTGCAGGCGCAGCCGCAGCCGCAGCTG
GAGGTGCTGGTCAAGGAGGATACGGAGGTCTTGGAAGCCAAGGTGCTGGACGAGGAGGATTAGGTGGA
CAAGGTGCAGGTGCAGCAGCAGCAGCTGGAGGTGTCGGACAAGGAGGACTAGGTGGACAAGGTGCTGG
ACAAGGAGCTGGAGCAGCTGCTGCAGCAGCTGGTGGTGCCGGACAAGGAGGATATGGAGGTCTCGGAA
GCCAAGGTGCAGGACGAGGTGGATCAGGTGGACAAGGGGCAGGTGCAGCAGCAGCAGCAGCTGGAGGT
GCCGGACAAGGAGGATATGGAGGTCTTGGAAGCCAAGGTGCAGGACGAGGTGGATTAGGTGGACAGGG
TGCAGGTGCAGCAGCAGCAGCAGCAGCCGGAGGTGCTGGACAAGGAGGATACGGTGGTCTTGGTGGAC
AAGGTGCCGGACAAGGTGGCTATGGAGGACTTGGAAGCCAAGGTGCTGGACGAGGAGGATTAGGTGGA
CAAGGTGCAGGTGCAGCAGCAGCAGCTGGAGGTGCCGGACAAGGAGGACTAGGTGGACAAGGAGCTGG
AGCAGCCGCTGCAGCAGCTGGTGGTGCCGGACAAGGAGGATATGGAGGTCTTGGAAGCCAAGGTGCTG
GACGAGGTGGACAAGGTGCAGGCGCAGCCGCAGCAGCAGCCGGAGGTGCTGGACAAGGAGGATACGGT
GGACAAGGTGCCGGACAAGGAGGCTATGGAGGACTTGGAAGCCAAGGTGCTGGACGAGGAGGATTAGG
TGGACAAGGTGCAGGTGCAGCAGCAGCAGCAGCAGCTGCAGGTGCCGGACAAGGAGGATTAGGTG
GACAAGGTGCAGGTGCAGCAGCAGCAGCAGCTGGAGGTGCTGGACAAGGAGGATTAGGTGGACAAGGT
GCTGGACAAGGAGCTGGAGCAGCCGCTGCAGCAGCCGCTGCAGCAGCTGGTGGTGTTAGACAAGGAGG
ATATGGAGGTCTTGGAAGCCAAGGTGCTGGACGAGGTGGACAAGGTGCAGGCGCAGCCGCAGCAGCAG
CCGGAGGTGCTGGACAAGGAGGATATGGTGGTCTTGGTGGACAAGGTGTTGGACGAGGTGGATTAGGT
GACAAGGTGCAGGCGCAGCGGCAGCTGTTGGTGCTGGACAAGGAGGATGGTGGTGTTGGTTCTGGGG
CGTCTGCTGCCTCTGCAGCTGCATCCCGTTTGTCTTCTCCTCAAGCTAGTTCAAGAGTTTCATCAGCTGTT
TCCAACTTGGTTGCAAGTGGTCCTACTAATTCTGCGGCCTTGTCAAGTACAATCAGTAATGTGGTTTCAC
AAATAGGCGCCAGCAATCCTGGTCTTTCTGGATGTGATGTCCTCATTCAAGCTCTTCTCGAGCACCACCA
CCACCACCACTGAA

FIG. 7

```
MASMTGGQQMGRIRIRGYGGLGGQGAGQGAGAAAAAAAGGAGQGGYGGLGSQGAGRGGQGAGAAAAA
AGGAGQGGYGGLGSQGAGRGGLGGQGAGAAAAAGGVGQGGLGGQGAGQGAGAAAAAAGGAGQGGYG
GLGSQGAGRGGSGGQGAGAAAAAAGGAGQGGYGGLGSQGAGRGGLGGQGAGAAAAAAGGAGQGGYG
GLGGQGAGQGGYGGLGSQGAGRGGLGGQGAGAAAAAGGAGQGGLGGQGAGAAAAAAGGAGQGGYGGL
GSQGAGRGGQGAGAAAAAGGAGQGGYGGQGAGQGGYGGLGSQGAGRGGLGGQGAGAAAAAAAGGA
GQGGLGGQGAGAAAAAGGAGQGGLGGQGAGQGAGAAAAAAAAAGGVRQGGYGGLGSQGAGRGGQ
GAGAAAAAAGGAGQGGYGGLGGQGVGAGGLGGQGAGAAAAVGAGQGGYGGVGSGASAASAAASRLSS
PQASSRVSSAVSNLVASGPTNSAALSSTISNVVSQIGASNPGLSGCDVLIQALLGHHHHH
```

FIG. 8

```
AEIYNKDGNKVDLYGKAVGLHYFSKGNGENSYGGNGDMTYARLGFKGETQINSDLTGYGQWEY
NFQGNNSEGADAQTGNKTRLAFAGLKYADVGSFDYGRNYGVVYDALGYTDMLPEFGGDTAYSD
DFFVGRVGGVATYRNSNFFGLVDGLNFAVQYLGKNERDTARRSNGDGVGGSISYEYEGFGIVGAY
GAADRTNLQEAQPLGNGKKAEQWATGLKYDANNIYLAANYGETRNATPITNKFTNTSGFANKTQ
DVLLVAQYQFDFGLRPSIAYTKSKAKDVEGIGDVDLVNYFEVGATYYFNKNMSTYVDYIINQIDS
DNKLGVGSDDTVAVGIVYQFA
```

FIG. 9

```
ATGAGAGGATCGCATCACCATCACCATCACGGATCCATGGCTAGCGGTGACCTGAAAAACAA
AGTGGCCCAGCTGAAAAGGAAAGTTAGATCTCTGAAAGATAAAGCGGCTGAACTGAAACAAG
AAGTCTCGAGACTGGAAAATGAAATCGAAGACCTGAAAGCCAAAATTGGTGACCTGAATAAC
ACTAGTGGGATCCGTCGACCTGCAGCCAAGCTTAATTAG
```

FIG. 10

```
MRGSHHHHHHGSMASGDLKNKVAQLKRKVRSLKDKAAELKQEVSRLENEIEDLKAKIGDLNNTSGIRRPAA
KLN
```

FIG. 11 pETNcDS fiber under light microscopy. Spun from 25% protein solution into 90% methanol coagulation bath.
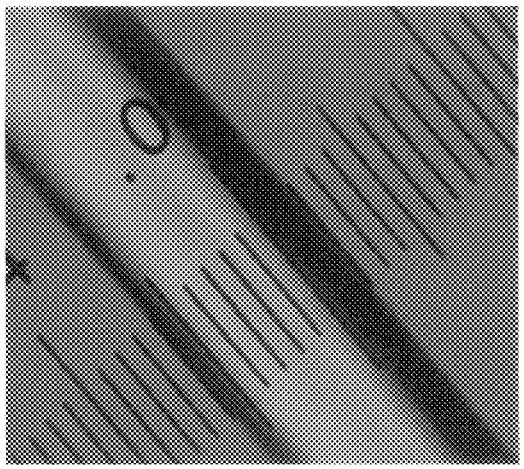 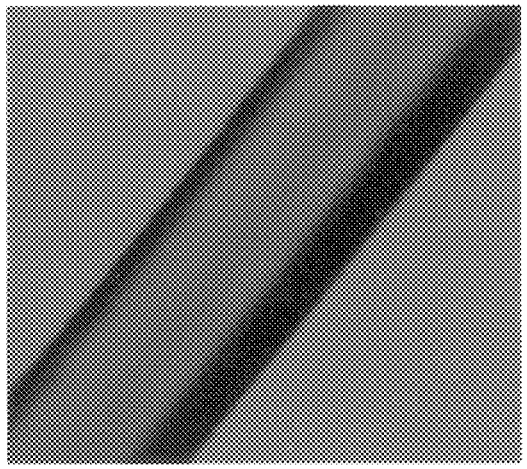
Polarized light w/tint plate
FIG. 17 pQE[(SP1)$_4$/(SP2)$_1$]$_4$ fiber under light microscopy. Spun from a 12.5% protein solution into 90% methanol coagulation bath.

White light        Polarized light w/ tint plate

METHOD FOR THE PURIFICATION AND AQUEOUS FIBER SPINNING OF SPIDER SILKS AND OTHER STRUCTURAL PROTEINS

STATEMENT OF GOVERNMENTAL INTEREST

The present invention may be used or licensed by the United States Government for Governmental purposes without the payment of any royalty.

FIELD OF THE INVENTION

The present invention relates to methods for purifying and spinning spider silks and other structural proteins. Specifically, organic acids are used to lyse recombinant cells or other biological samples (such as non-recombinantly derived cells), and significantly enrich the purity and yields of structural proteins by hydrolyzing many of the macromolecules, while leaving the structural proteins intact. In the case of silk proteins, the resulting lysate is further purified by ion-exchange or affinity chromatography and processed into an aqueous-based mixture for fiber spinning.

BACKGROUND

Spiders produce a number of silks for different functions and are therefore useful organisms to produce a variety of structural proteins. The structural fibers of the golden orb-weaver spider (Nephila clavipes), are extremely strong and flexible, and are able to absorb impact energy from flying insects without breaking. Dragline silk fibers dissipate energy over a broad area and balance stiffness, strength and extensibility. In addition, silk proteins have very low antigenicity. Therefore, silk fibers are well suited for light weight, high performance fiber, composite and medical applications. The composition of these proteins is mainly glycine, alanine, and other short side chain amino acids, which form anti-parallel beta-pleated sheets by hydrogen bonding and hydrophobic interactions; Lucas et al., Discovery 25:19 1964. Many spider silks are resistant to digestion by proteolytic enzymes; Tillinghast and Kavanaugh, Journal of Zoology 202:212 1977, and insoluble in dilute acids and bases; Mello et al., American Chemical Society Symposium Series 544, Silk Polymers: Materials, Science and Biotechnology pp 67–79, 1995. Spiders are not capable of producing sufficient quantities of proteins to enable a practical use of their potential. To solve this problem, recombinant spider silks have been expressed in E.coli; Arcidiacono et al., Applied Microbiology and Biotechnology 49:31 1998; Fahnestock and Irwin, Applied Microbiology and Biotechnology 47:23, 1997; Fahnestock and Irwin, Applied Microbiology and Biotechnology 47:33 1997; Lewis et al., Protein Expression and Purification 7:400, 1996; Prince et al., Biochemistry 34:10879 1995. However, the purification and preparation of a protein for fiber spinning has been particularly difficult due to the solubility characteristics and unique properties of spider silk and other structural proteins.

Native Nephila clavipes spider dragline fiber has been partially solubilized in hexafluoroisopropanol (HFIP) and dried to a film. A 2.5% (w/w) solution of the film in HFIP was used for spinning; Jelinski et al., Macromolecules 31:6733 1998. The spinning was conducted with a syringe pump at 6 uL/s by forcing the HFIP solution through the spinneret into a coagulation bath.

Affinity chromatography has been used for purification by binding to an engineered tag in the recombinant protein while washing away bacterial proteins; Arcidiacono et al., Applied Microbiology and Biotechnology 49:31 1998; Fahnestock and Irwin, Applied Microbiology and Biotechnology 47:23 1997; Lewis et al., Protein Expression and Purification 7:400 1996; Prince et al., Biochemistry 34:10879 1995. One commonly used tag is a hexa-histidine tag, that binds with high affinity to a nickel affinity resin. After washing away the bacterial proteins, the tagged recombinant protein can be eluted from the resin. There are several disadvantages to this method: 1) large volumes of denaturing buffers are required, involving multiple steps and time; 2) not all target protein is recovered; 3) other bacterial proteins remain, often requiring additional purification (i.e., high-performance liquid chromatography (HPLC)); 4) the method is not easily scaled-up; 5) and the presence of an affinity tag on the recombinant protein may increase its antigenicity and interfere with the necessary molecular alignment required for high strength fibers. Accordingly, there is a continuing need to develop new methods for the purification of structural proteins, spinning of silk fibers lacking the engineered tag and enabling the assembly of macromolecular structures without potential interferences.

SUMMARY OF THE INVENTION

As a solution to the above-related deficiencies in the prior art, the present invention contemplates using organic acids to purify recombinant spider silks or other non-recombinant structural proteins from E. coli bacteria while removing the unwanted bacterial proteins. The invention is based on the unique solubilization and stability characteristics of these proteins, which are resistant to acid hydrolysis for prolonged periods of time at room temperature, while many globular proteins are not. Purified protein solutions can be processed into a spinnable aqueous-based mixture for the production of fibers. The present invention also contemplates an aqueous protein spinning method that closely mimics the natural spinning process of the spider and has the potential to produce fibers with properties that may resemble or improve upon those of natural silk fibers. The present invention represents the first known example of an aqueous process for the spinning of silk proteins into fibers. Furthermore, this invention is the only known report, to date, of spinning recombinant silk proteins into fibers. The present invention displays numerous advantages over the background art, including a purification method with organic acids containing fewer steps, requiring less time and smaller volumes of reagents. The present invention also results in better recovery of protein at a higher purity. For example, the $(SP1)_7$ protein can be recovered at a level of 150 mg/L, compared to the 7mg/L recovery rate by the current art (see Prince et al., supra). While not limited to any mechanism by which a recovery is achieved, it is believed that lower protein recovery rates by the traditional methods are caused, in part, from incomplete binding of the protein to the affinity resin. Such traditional techniques include, but are not limited to, ion exchange chromatography and affinity chromatography. The inability of these proteins to bind to the resin is most likely due to a high degree of secondary structure even in the presence of high concentrations of denaturant. Sample purity from the present invention has been obtained in the range of 94–97% as determined by amino acid analysis (see Examples 1 and 2, infra). The current art results in a wide and inconsistent range of purity ranging from 70% (Prince et al., supra), to 99% (Lewis et al., 1996, supra). While high sample purity is possible using current art by affinity chromatography, the presence of the histidine affinity tag significantly increases the antigenicity of the protein and adversely affects the properties of fibers, films, or other materials by disrupting the proper molecular orientation required within the material. Also, in many cases the current art results in samples still contaminated by other bacterial proteins, requiring additional purification such as HPLC (Prince et al.; Lewis et al., supra). Finally, the methods of the present invention are easily scaled-up, and fibers are spun in an environmentally benign solution reducing hazardous waste accumulation and cost. For example, the present invention contemplates the spinning of silk proteins in an environmentally innocuous aqueous based system. In one embodiment of the present invention, a solution of an organic acid is used to effect the lysis of bacteria and initiate purification of recombinant silks and native structural proteins. Globular proteins are hydrolyzed while the silk protein remains intact. Silk proteins remain and are concentrated into an aqueous-based mixture for fiber spinning. The embodiment may comprise the following steps: a) resuspension of the cell pellet in concentrated organic acid and dilution to 2.3N in water (+/−denaturant and/or surfactant) to form a homogeneous mixture; b) incubation at room temperature 1 hour with stirring and centrifugation to remove cell debris; c) reduction of volume, 10–100 fold by ultrafiltration and removal of insoluble material by centrifugation; d) dialysis and removal of insoluble material by centrifugation; e) purification by ion exchange chromatography and dialysis into processing buffer; f) concentration of solution to 11–40% (w/w) protein by ultrafiltration and spinning solution into fibers. While this embodiment is given for guidance, those of skill in the art may choose to add or delete certain steps while remaining within the spirit and scope of the present invention. For example, the purification methodology may be employed with or without the spinning of the fiber solution. Several native and recombinant structural proteins have been purified by this method. Any biological sample containing a structural protein of interest, native or recombinant, is amenable to the methodology outlined in the invention. Examples of biological samples may include, but are not limited to, E. coli cells, other bacterial cells, eukaryotic cells, a medium in which a structural protein has been secreted, bone, tissues or organs. And while many variables have been examined and optimized throughout the process, each variable and optimization exemplify variations of the overall general method. Choosing among the various parameters is highly dependent on the protein being prepared. Table 1 below lends guidance to those of skill in the art.

TABLE 1

| Variables Explored | Conclusion |
| --- | --- |
| Lysis | |
| 1. Type of acid | Protein: (4 + 1)$_4$ Acid: Propionic |
| | Protein: (Spl)$_7$ Acid: Formic |
| | Protein: NcDS Acid: Formic |
| | Protein: OmpF Acid: Valeric |
| | Protein: Recognin Acid: Valeric |
| 2. Volume acid/g cells (2–100 ml/g) | Increased acid volume generally decreases purity |
| 3. Acid strength (0.5–23N) | Full strength is best (23N Formic, 13N Propionic) for lysis. |
| 4. Length of lysis (30 min-overnight) | 1 hr is preferred |
| 5. Temperature of lysis (25° C.–37° C.) | No effect |
| 6. Lysis under denaturing conditions | Solubility improves, purity decreases |
| 7. Lysis in the presence of detergents | No effect on purity |

TABLE 1-continued

| Variables Explored | Conclusion |
| --- | --- |
| Purification | |
| 1. Lysate purification by chromatography Processing | Chromatography successfully purifies target (affinity, ion exchange). |
| 1. Urea concentration in the processing buffer (160 mM vs 1M) | 1M urea improves solubility slightly |
| 2. Ionic strength of the processing buffer (20–100 mM NaCl) | Increasing NaCl concentration causes precipitation |
| Spinning | |
| 1. Spin aqueous-based mixture protein concentration (11–35%) | Protein dependent |
| 2. Age of aqueous-based mixture (0–5 days) | Spinnability changes as the aqueous-based mixture ages |
| 3. Temperature during aging (4–30° C.) | Higher temperatures accelerate changes in the solution behavior (i.e. spinnability and solubility) |
| 4. Coagulation bath (70–90% methanol) | Methanol percentage affects speed of fiber formation, fiber behavior |

A variety of embodiments are contemplated. In one embodiment, the present invention contemplates a method, comprising: a) providing: i) a biological sample comprising one or more structural polypeptides; and ii) an acid; b) treating said sample with said acid under conditions such that said one or more polypeptides is recovered in a solution. A variety of structural peptides are contemplated, including but not limited to polypeptides selected from SEQ ID NO.: 2, SEQ ID NO.: 4, SEQ ID NO.: 6, SEQ ID NO.: 8, SEQ ID NO.:9, and SEQ ID NO.: 11. the peptides may be recombinant or native polypeptides.

A variety of acids are contemplated. Organic acids are preferred. In one embodiment, the present invention contemplates one or more organic acids selected from formic, acetic, propionic, butyric, and valeric acids.

It is the goal to produce fibers. Therefore, in one embodiment, the method further comprises the step of manipulating said solution under conditions such that insoluble fibers are produced. Indeed, the present invention specifically contemplates the fibers produced according to the above-described process.

The present invention specifically contemplates methods wherein recombinant structural proteins are manipulated. In one embodiment, the present invention contemplates a method, comprising: a) providing: i) host cells expressing one or more recombinant structural polypeptides, and ii) a solution comprising an organic acid; b) treating said host cells with said solution to create a mixture; c) removing insoluble material from said mixture; and d) recovering said one or more recombinant polypeptides in a solution. Again, a variety of peptides are contemplated. In one embodiment, one or more polypeptides are selected from SEQ ID NO.: 2, SEQ ID NO.: 4, SEQ ID NO.: 6, SEQ ID NO.: 8, SEQ ID NO.:9, and SEQ ID NO.: 11. Again, a variety of acids are contemplated, including but not limited to organic acids selected from formic acid, acetic acid, propionic acid, butyric acid, and valeric acid.

To produce fibers, the method involves manipulation of said recovered one or more recombinant polypeptides in said solution under conditions such that insoluble fibers are produced. The present invention specifically contemplates the fibers themselves produced according to the above-described process.

A variety of host cells are contemplated for recombinant production. Thus, in one embodiment the present invention contemplates a method, comprising: a) providing: I) bacterial cells expressing one or more recombinant structural polypeptides, and ii) a solution comprising an organic acid selected from formic acid, acetic acid, propionic acid, butyric acid, and valeric acid; b) treating said bacterial cells with said solution to create a mixture; c) removing insoluble material from said mixture; and d) recovering said one or more recombinant polypeptides in a solution. As noted above, a variety of peptides are contemplated, including but not limited to one or more polypeptides is selected from SEQ ID NO.: 2, SEQ ID NO.: 4, SEQ ID NO.: 6, SEQ ID NO.: 8, and SEQ ID NO.: 11.

To produce fibers, said recovered one or more recombinant polypeptides are manipulated under conditions such that insoluble fibers are produced. In a preferred embodiment, said manipulating comprises: a) concentrating said recovered one or more recombinant silk polypeptides to create a concentrated solution; and b) forcing said concentrated solution through a spinneret. The present invention specifically contemplated the fibers themselves which are produced according to this process.

In sum, the present invention contemplates a method, which comprises providing a biological sample composed of a polypeptide and an acid, and manipulating the biological sample under conditions such that the polypeptide is substantially purified into an aqueous-based mixture.

The method, in several embodiments, includes using polypeptides that may be selected from SEQ ID NO.: 2, SEQ ID NO.: 4, SEQ ID NO.: 6, SEQ ID NO.: 8, SEQ ID NO.: 9, and SEQ ID No.: 11 herein, although other amino acid sequences are also contemplated.

In another embodiment of the present invention, the biological sample comprises many types of polypeptides, including, but not limited to, recombinant and non-recombinant polypeptides. Structural polypeptides, such as silk polypeptides, are also contemplated.

In further embodiments of the present invention, organic acids are used to manipulate aqueous-based mixtures under conditions such that the mixtures may be processed into fibers. The organic acids that may be used include, but are not limited to, formic, acetic, propionic, butyric, and valeric acids. The present invention further contemplates the product that is achieved by the methods that are described herein.

While a variety of applications for the methods and products herein described are contemplated, the applications are not limited. For example, the compositions of the present invention may comprise any type of replacement for, or blended with, high strength light-weight synthetic polymers (e.g., kevlar®) for applications such as manufacture of skis, skateboards, and tennis rackets. The method of the present invention can also be used to create a product that can be used as a precursor to the construction of many materials, including, but not limited to, films, fibers, woven articles (e.g., clothing), sutures, ballistic protection, parachutes and parachute cords.

DESCRIPTION OF THE DRAWINGS

The file of this patent contains at least one drawing executed in color. Copies of this patent with color drawings will be provided by the Patent and Trademark Office upon request and payment of the necessary fee.

To facilitate an understanding of the invention, a number of Figures are included herein.

FIG. 1 presents the nucleic acid sequence of a recombinant silk protein (SEQ ID NO: 1) designated pQE(sp1)$_7$.

FIG. 2 presents a recombinant silk protein (SEQ ID NO: 2), designated pQE(SP1)$_7$, that is the gene product of the nucleic acid sequence presented in (SEQ ID NO: 1).

FIG. 3 presents the nucleic acid sequence of a recombinant silk protein (SEQ ID NO: 3) designated pQE[(SP1)$_4$/(SP2)$_1$]$_4$.

FIG. 4 presents a recombinant silk protein (SEQ ID NO: 4), designated pQE[(SP1)$_4$/(SP2)$_1$]$_4$, that is the gene product of the nucleic acid sequence presented in (SEQ ID NO: 3).

FIG. 5 presents the nucleic acid sequence of a recombinant silk protein (SEQ ID NO: 5) designated pET[(SP1)$_4$/(SP2)$_1$]$_4$.

FIG. 6 presents a recombinant silk protein (SEQ ID NO: 6), designated pET[(SP1)4/SP2)$_1$]$_4$ that is the gene product of the nucleic acid sequence presented in (SEQ ID NO: 5).

FIG. 7 presents the nucleic acid sequence of a recombinant silk protein (SEQ ID NO: 7) designated pETNcDS.

FIG. 8 presents a recombinant silk protein (SEQ ID NO: 8), designated pETNcDS, that is the gene product of the nucleic acid sequence presented in (SEQ ID NO: 7).

FIG. 9 presents a bacterial membrane protein (SEQ ID NO: 9), designated ompF.

FIG. 10 presents the nucleic acid sequence of a recombinant structural protein. (SEQ ID NO: 10) designated Recognin B1.

FIG. 11 presents a recombinant structural protein (SEQ ID NO: 11), designated Recognin B1, that is the gene product of the nucleic acid sequence presented in (SEQ ID NO: 10).

FIG. 17 presents photomicrographs of a pETNcDS fiber spun from a protein solution of 25% (w/v) as determined by extinction coefficient. Fibers were generated at a rate of at 10 ul/min in a 90% methanol coagulation bath. Consistent diameters of about 60 urn were observed. Under polarizing light, the color changed uniformly from blue to yellow as the angle of light was changed indicating directional orientation in the fiber.

DEFINITIONS

Figure 12:
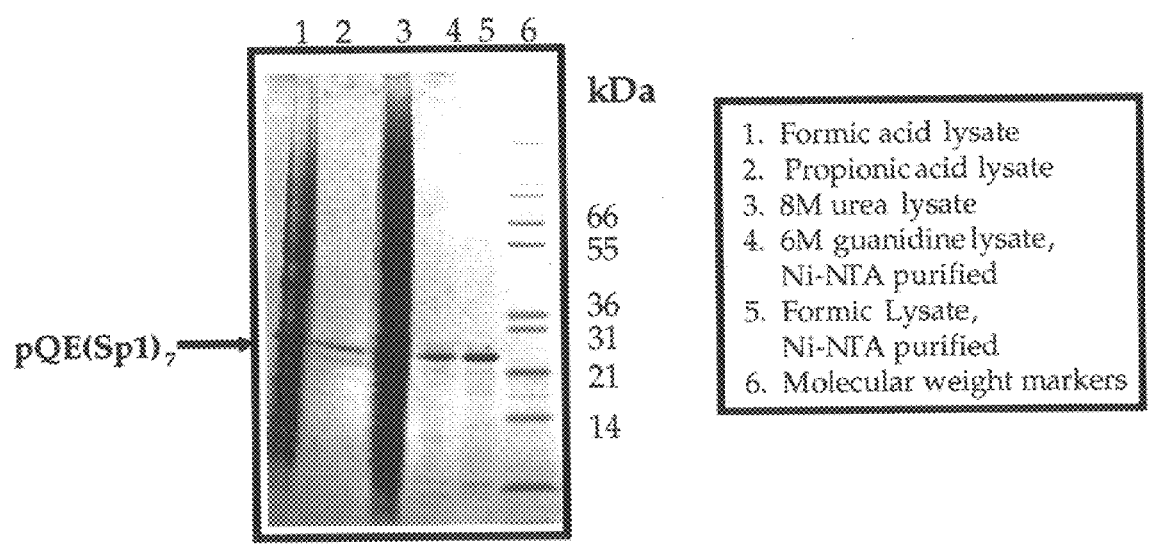
FIG. 12 presents a polyacrylamide gel comparing acid lysis purification of the recombinant silk protein pQE(Sp1)$_7$ to traditional denaturing method. The pQE(Sp1)$_7$ protein is enriched by acid lysis compared to lysis under denaturing conditions (e.g. 8M urea). Subsequent affinity chromatography purification by Ni-NTA of the formic acid lysate results in a yield comparable to the purification of the traditional denaturing lysate.

To facilitate an understanding of the invention, a number of terms are defined.

The term "aqueous", as defined herein, refers to a water miscible solution.

The term "aqueous-based mixture", as defined herein, refers to a protein in an aqueous solution. The mixture may be used for protein purification, fiber spinning, film formation or other materials.

The term "aqueous fiber spinning" refers to a process by which fibers are formed from an aqueous solution.

The terms "spin" "spinnable" as used herein, refers to a mixture that is capable of forming a fiber and the fiber remains intact during manipulation (i.e. drawing and removal from a coagulation bath).

The term "biological sample", as defined herein, refers to any sample containing a structural protein of interest, native or recombinant, that is amenable to the methodology of the present invention. Examples of biological samples may include, but are not limited to, *E. coli* cells, other bacterial cells, eukaryotic cells, a medium where the structural protein has been secreted, bone, tissues or organs.

The term "recombinant protein", as used herein, refers to the product produced by expression of a recombinant DNA sequence in a foreign host. The (Sp1)7 protein, described herein in Example 1, exemplifies a recombinant protein.

The term "recombinant" or "recombining" refers to a nucleic acid sequence which is incorporated into a vector, e.g., into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment) independent of other DNA sequences. This definition also includes recombinant DNA which is part of a hybrid gene encoding additional amino acid sequences.

The term "recombinant DNA vector" as used herein refers to DNA sequences containing a desired coding sequence and appropriate DNA sequences necessary for the expression of the operably linked coding sequence in a particular host organism (e.g., bacteria). DNA sequences necessary for expression in prokaryotes include a promoter, optionally an operator sequence, a ribosome binding site and possibly other sequences. Eukaryotic cells are known to utilize promoters, polyadenylation signals and enhancers.

The term "non-recombinant" refers to proteins that are derived by other than recombinant means. Non-recombinant protein may be structural or non-structural. The *E. coli* OmpF membrane protein (described herein in Example 6), which is, in this case, a naturally occurring protein that serves as an example of a non-recombinant protein.

The term "lyophilized pellet" represents a sample that is derived from a biological sample where the sample is frozen and dried under vacuum (−50° C. & 10–100 microns of Hg) to produce a powder.

The term "purified" or a "pure preparation" of a polypeptide, as used herein, means a polypeptide that has been separated from other proteins, lipids, and nucleic acids with which it naturally occurs. The polypeptide is also separated from substances, e.g., antibodies or gel matrix, e.g., polyacrylamide, which are used to purify it. The term "substantially purified" polypeptide of the present invention constitutes at least 50%, and often above 90%, of the purified preparation as based on amino acid analysis.

The term "acid" for the purposes of the present invention, refers to any organic acid that is capable of hydrolyzing contaminating proteins while allowing silk or other structural proteins to remain intact. Formic, acetic, propionic, butyric, and valeric acids are all examples of organic acids, although other acids are also contemplated.

For the purposes of this invention, we define a "protein" as a polymer in which the monomers are amino acids and which are joined together through amide bonds and alternatively referred to as a polypeptide. The terms "protein" and "polypeptide" are herein used interchangeably. Standard abbreviations for amino acids are used (e.g., P for proline). These abbreviations are included in Stryer, Biochemistry, Third Ed., (1988), which is incorporated herein by reference for all purposes.

The term "silk polypeptide" refers to a protein that approximates the molecular and structural profile of native silk proteins and fibers.

The term "structural protein" or "structural polypeptide" refers to a class of non-catalytic proteins that may serve as a biological structural support. The proteins may serve as biological structural supports by themselves, in conjunction with other proteins, or as a matrix or support for other materials. Examples from this class include, but are not limited to, proteins such as spider silks, that are used for spider web architecture; porin proteins, which form channels in biological membranes; keratin, the major structural component of hair; collagen, the major extracellular protein in connective tissue. The silks, OmpF and recognin proteins described herein are examples of structural proteins.

The term "recovered" refers to the process by which protein is locally sequestered and captured.

The term "organic acid" refers to the class of acids, such as formic, acetic, propionic, butyric, and valeric acids, which are found in living organisms but not necessarily, derived from said living organism. Said organic acids can also be obtained from commercial vendors (e.g. Sigma Chemical).

As used herein, the term "host cell" refers to any cell capable of expressing a functional gene and/or gene product introduced from another cell or organism. This definition includes *E. coli.*, as well as other organisms.

The term "insoluble fibers" refers to proteinaceous fibers that will not solubilize in an aqueous solution.

The term "bacterial" refers to any of numerous groups of microscopic, one-celled organisms including, but not limited to the phylum Eubacteria of the kingdom Procaryotae.

The term "concentrating" refers to any process that increases the molarity of proteinaceous solution.

The term "concentrated solution" refers to a proteinaceous solution adjusted to a predetermined molarity higher than said pre-adjusted proteinaceous solution.

The term "spinneret" refers to a small orifice used for fiber formation.

DESCRIPTION OF THE INVENTION

A number of different embodiments, as exemplified in the examples, of the present invention are contemplated, including the scaling-up of the method, automation of the method, or use of the method to purify other structural proteins.

One of skill in the art will recognize that the practice of the present invention will employ, unless otherwise indicated, conventional techniques of cell biology, cell culture, molecular biology, microbiology, and recombinant DNA, which are within the skill of the art. Such techniques are described in the literature. See, for example, *Molecular Cloning, A Laboratory, Manual*, 2nd Ed., by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.).

The proteins of the present invention can be made by direct synthesis (chemically or biologically) or by expression from cloned DNA. The source of the protein is not limited to recombinant means. Non-recombinant proteins may be purified or spun using the methods described herein. Indeed, Example 6, infra, describes the purification of *E. coli* OmpF membrane protein, which is, in this case, a naturally occurring (i.e. non-recombinant protein) protein.

The means for expressing cloned DNA are generally known in the art. However, there are some considerations for design of expression vectors that are unusual for expressing DNA encoding the spider silk proteins of the present invention. For example, the proteins are highly repetitive in their structure. Accordingly, cloned DNA should be propagated and expressed in host cell strains that will maintain repetitive sequences in extrachromosomal elements (e.g. SURE™ cells, Stratagene). Also, due to the high content of alanine, glycine, proline, and glutamine, it might be advantageous to use a host cell which over expresses tRNA for these amino acids.

The present invention contemplates the use of many different organic acids to manipulate recombinant and non-recombinant biological samples under conditions such that a polypeptide is substantially purified. While the use of *E. coli* cells with formic, propionic and valeric acid are contemplated, the present invention is not limited to these particular embodiments, but may also be practiced using other organic acids, such as acetic, and butyric, acids, all of which serve as examples. The present invention may also be practiced using other prokaryotic or eukaryotic cells (aside from, or along with, *E. coli* cells), the media in which the protein-of-interest has been secreted, organs, tissue, bone and other components, all of which are examples of biological sample materials.

EXPERIMENTAL

The following examples serve to illustrate certain embodiments and aspects of the present invention and are not to be construed as limiting the scope thereof.

EXAMPLE 1

Purification of Recombinant Silk Protein with Formic Acid and Ion Exchange Chromatography In this example, the gene product of pQE(sp1)$_7$ (SEQ ID NO: 1), as set out in FIG. 1, is expressed as recombinant silk protein pQE(SP1)$_7$ (SEQ ID NO: 2), as set out in FIG. 2, in *E.coli* as described elsewhere (Prince et al., 1995). The (sp1)$_7$ gene was cloned into the expression vector pQE-9 (Qiagen) and transformed into the host cell line SG13009pREP4 (Stratagene). Cultures were grown to an $A_{600}$=1.5–2.0 in 4×YT medium (per liter: 32 g tryptone, 20 g yeast extract, 5 g NaCl) containing 400 ug/mL ampicillin. Protein expression was induced by the addition of isopropyl-thiogalactopyranoside (IPTG) to a final concentration of 1 mM. After 1–4 hours the cells were harvested by centrifugation and stored for purification. Lyophilized pellets were lysed in 23N formic acid (100 ml/g cell pellet), diluted to 4.6N acid with distilled and deionized water and stirred 1 hour at room temperature. The cell lysate was clarified by centrifugation and concentrated 20 fold by ultrafiltration. The solution was clarified by centrifugation and the supernatant was dialyzed extensively into 8M urea, 10 mM NaH$_2$PO$_4$, 1 mM Tris, 20 mM NaCl, pH 8. Precipitated material was removed by centrifugation and the clarified supernatant was applied to an affinity chromatography resin (nickel-NTA agarose) that had been equilibrated with 8M urea, 10 mM NaH$_2$PO$_4$, 1 mM Tris, 20 mM NaCl, pH 8. The chromatography conditions were designed to bind the recombinant silk protein, but let the remaining bacterial proteins pass through the column. The column was washed with 8M urea, 10 mM NaH$_2$PO$_4$, 1 mM Tris, 20 mM NaCl, pH 7. The pQE(SP1)$_7$ protein was eluted from the column 8M urea, 10 mM NaH$_2$PO$_4$, 1 mM Tris, 20 mM NaCl, pH 3.The sample was 94% pure as determined by quantitative amino acid analysis. FIG. 12 illustrates a comparison of traditional purification techniques with the methodology enclosed in this application. Cells lysed with formic acid yielded more silk protein with a similar purity when compared to the 6M guanidine lysis with Ni-NTA affinity chromatography.

EXAMPLE 2

Purification of Recombinant Silk Protein with Propionic Acid and Ion Exchange Chromatography In this example, the gene product of pQE[(SP1)$_4$/(SP2)$_1$]$_4$ (SEQ ID NO: 3), as set out in FIG. 3, is expressed as recombinant silk protein pQE[(SP1)$_4$/(SP2)$_1$]$_4$ (SEQ ID NO: 4), as set out in FIG. 4, in *E.coli* (Prince et al., 1995). The [(SP1)$_4$/(SP2)$_1$]$_4$ gene was cloned into the expression vector pQE-9 (Qiagen) and transformed into the host cell SG13009pREP4 (Stratagene). Cultures were grown to an $A_{600}$=1.5–2.0 in 4×YT medium (per liter: 32 g tryptone, 20 g yeast extract, 5 g NaCl) containing 400 ug/mL ampicillin. Protein expression was induced by the addition of IPTG to a final concentration of 1 mM. After 1–4 hours the cells were harvested by centrifugation and stored for purification. Lyophilized pellets were lysed in 13.3N propionic acid (2 ml/g cell pellet), diluted to 2.3N acid with distilled and deionized water and stirred 1 hour at room temperature. The cell lysate was clarified by centrifugation and concentrated 20 fold by ultrafiltration. Many of the acid stable proteins became insoluble and were removed by centnifugation. The clarified supernatant was dialyzed extensively into 10 mM Tris, pH 9 containing 2M urea. The dialyzed solution was applied to a strong anion exchange resin, QAE-Sephadex A50, that had been equilibrated with 10 mM Tris, pH 9 containing 2M urea. The chromatography conditions were designed such that the positively charged silk protein would not bind to the column, but the remaining proteins with lower isoelectric points and net negative charge would bind to the column. The column was washed with 10 mM Tris, pH 9 containing 2M urea to recover any remaining silk protein. The wash was pooled with the unbound silk containing fraction and processed. The sample was 97% pure as determined by quantitative amino acid analysis.

EXAMPLE 3

Figure 13:
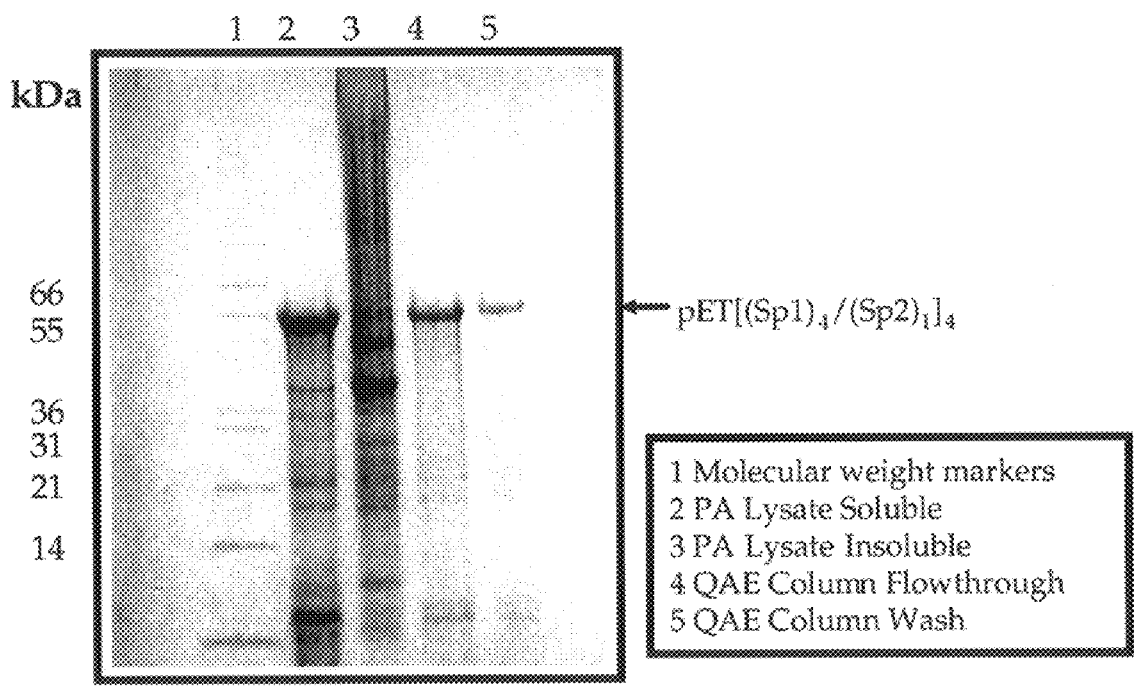
FIG. 13 represents a polyacrylamide gel depicting the QAE-Sephadex purification scheme with a propionic acid extracted pET[(Sp1)$_4$/(Sp2)$_1$]$_4$ protein sample.

Purification of Recombinant Silk Protein with Propionic Acid and Ion Exchange Chromatography In this example, the gene product of pET[(SP1)$_4$/(SP2)$_1$]$_4$ (SEQ ID NO: 5), as set out in FIG. 5, is expressed as recombinant silk protein pET[(SP1)$_4$/(SP2)$_1$]$_4$ (SEQ ID NO: 6), as set out in FIG. 6, in *E.coli* (Prince et al., 1995). The [(SP1)$_4$/(SP2)$_1$]$_4$ gene was cloned into the expression vector pET24 (Novagen Inc.) and transformed into the host cell BL21(DE3) pLysS. Cultures were grown to an $A_{600}$=19 in defined medium (per liter: 13.3 g KH$_2$PO$_4$, 4 g (NH$_4$)$_2$HPO$_4$, 1.7 g Citric acid, 25 g glucose, 1,2 g MgSO$_4$-7H$_2$O, 39 mg FeCl$_3$, 13 mg MnSO$_4$-H$_2$O, 10 mg ZnSO$_4$-7H$_2$O, 3 mg H$_3$BO$_3$, 2.5 mg Na$_2$MoO$_4$-2 H$_2$O, 2.5 mg CoCl$_2$-6H$_2$O, 1.8 mg Cu(CH$_3$COO)$_2$-H$_2$O, 6.7 mg EDTA, 4.5 mg thiamine-HCl) with kanamycin (30 ug/ml) at 37° C., 16 liter/min air and 600 rpm. Expression was induced for 1 hr with 1 mM IPTG at which time the cells were harvested by centrifugation and stored for purification. Lyophilized pellets were lysed in 13.3N propionic acid (2 ml/g cell pellet), diluted to 2.3N acid with distilled and deionized water and stirred 1 hour at room temperature. The cell lysate was clarified by centrifugation and concentrated 20 fold by ultrafiltration. Many of the acid stable proteins became insoluble and were removed by centrifugation. The clarified supernatant was dialyzed extensively into 10 mM Tris, pH 9 containing 2M urea. The dialyzed solution was applied to a strong anion exchange resin QAE-Sephadex A50 that had been equilibrated with 10 mM Tris, pH 9 containing 2M urea. The chromatography conditions were designed such that the positively charged silk protein would not bind to the column, but the remaining proteins with lower isoelectric points and net negative charge would bind to the column. The column was washed with 10 mM Tris, pH 9 containing 2M urea to recover any remaining silk protein. The wash was pooled with the unbound silk containing fraction and processed. The sample was 75–85% pure as determined by coomassie-blue staining of a polyacrylamide gel (see FIG. 13).

EXAMPLE 4

Figure 14:
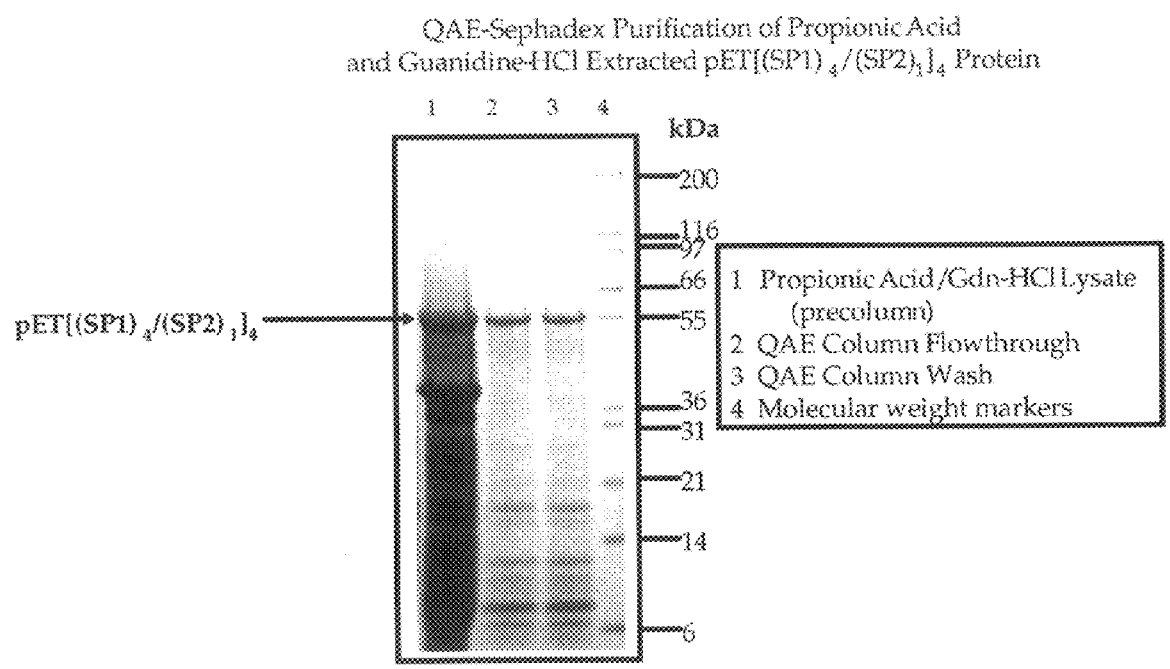
FIG. 14 presents a polyacrylamide gel depicting the purification of pET[(Sp1)$_4$/(Sp2)$_1$]$_4$ by lysis with propionic acid with 3M guanidine-HCl and ion-exchange chromatography using QAE-Sephadex A50.

Purification of Recombinant Silk protein with Propionic Acid Containing Denaturant and Ion Exchange Chromatography In this example, the gene product of pET[(SP1)$_4$/(SP2)$_1$]$_4$ (SEQ ID NO: 5), as set out in FIG. 5, is expressed as recombinant silk protein pET[(SP1)$_4$/(SP2)$_1$]$_4$ (SEQ ID NO: 6), as set out in FIG. 6, in *E.coli* (Prince et al., 1995). Lyophilized pellets were lysed in 13.3N propionic acid (2 mL/g cell pellet), diluted to 2.3N acid with 6M guanidine hydrochloride (to a final concentration of 3M) and distilled and deionized water and stirred for 1 hour at room temperature. The cell lysate was clarified by centrifugation and concentrated 3 fold by ultrafiltration. Precipitated material was removed by centrifugation and the clarified supernatant was dialyzed extensively into 10 mM Tris, pH 9 containing 2M urea. Many of the acid stable proteins became insoluble and were removed by centrifugation. The dialyzed supernatant was applied to a strong anion exchange resin, QAE-Sephadex A50 that had been equilibrated with 10 mM Tris, pH 9 containing 2M urea. The chromatography conditions were designed such that the positively charged silk protein would not bind to the column, but the remaining proteins with lower isoelectric points and net negative charge would bind to the column. The column was washed with 10 mM Tris, pH 9 containing 2M urea to recover any remaining silk protein (see FIG. 14). The wash was pooled with the unbound silk containing fraction and processed as describe in example 9. This sample was approximately 80% pure based on coomassie blue staining.

EXAMPLE 5

Purification of Recombinant Silk Protein with Formic Acid Containing Denaturant and Affinity Chromatography In this example, the gene product of pETNcDS (SEQ ID NO: 7), as set out in FIG. 7, is expressed as recombinant silk protein pETNcDS (SEQ ID NO: 8), as set out in FIG. 8, in *E.coli* (Arcidiacono et al. 1998). The NcDS gene was cloned into the expression vector pET24 (Novagen Inc.) and transformed into the host cell BL21(DE3) pLysS. Cultures were grown to an $A_{600}$=4 in 4×YT medium (per liter: 32 g tryptone, 20 g yeast extract, 5 g NaCl) with kanamycin (30 ug/ml)at 37° C., 1 liter/min air and 800 rpm. Expression was induced for 3 hr with 1 mM IPTG at which time the cells were harvested by centrifugation and stored for purification. Lyophilized pellets were lysed in 23N formic acid (5 ml/g cell pellet), diluted to 2.3N acid with 6M guanidine hydrochloride (to a final concentration of 3M) and distilled and deionized water and stirred 1 hour at room temperature. The cell lysate was clarified by centrifugation and concentrated 20 fold by ultrafiltration. The solution was clarified by centrifugation and the supernatant was dialyzed extensively into 8M urea, 10 mM NaH$_2$PO$_4$, 1 mM Tris, 20 mM NaCl, pH 8. Precipitated material was removed by centrifugation and the clarified supernatant was applied to an affinity chromatography resin (nickel-NTA agarose) that had been equilibrated with 8M urea, 10 mM NaH$_2$PO$_4$, 1 mM Tris, 20 mM NaCl, pH 8. The chromatography conditions were designed to bind the recombinant silk protein, but let the remaining bacterial proteins pass through the column. The column was washed with 8M urea, 10 mM NaH$_2$PO$_4$, 1 mM Tris, 20 mM NaCl, pH 7. The NcDS protein was eluted from the column 8M urea, 10 mM NaH$_2$PO$_4$, 1 mM Tris, 20 mM NaCl, pH 3. The purified protein could then be processed for fiber spinning as in Example 8.

EXAMPLE 6

Valeric Acid Purification of *E. coli* OmpF Membrane Protein

Figure 15:
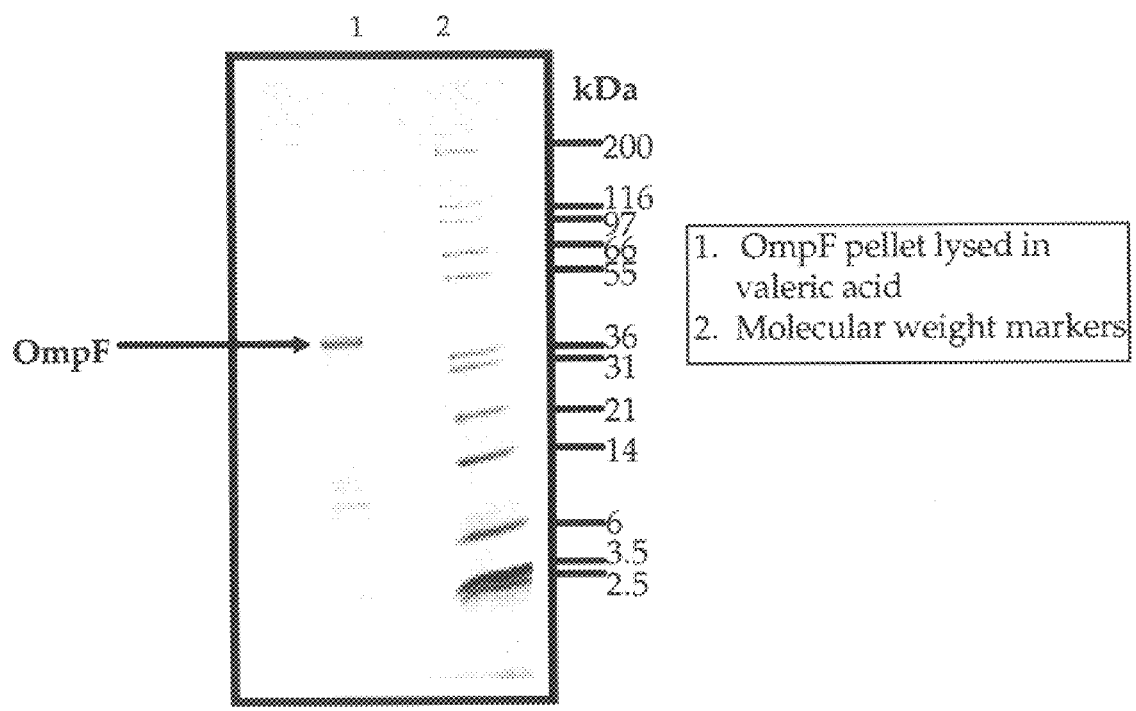
FIG. 15 represents a polyacrylamide gel depicting the purification of ompF, a native *E. coli* structural protein from a lyophilized *E. coli* cell pellet. The cell pellet was extracted using valeric acid. This extraction procedure yielded a purity of approximately 85% based on coomassie-blue staining.

In this example, a native *E. coli* ompF membrane protein (SEQ ID NO: 9), as presented in FIG. 9, was purified. Cells were grown and harvested as described in Example 3. Because OmpF is a native *E. coli* protein, its production was not induced by the addition of IPTG. Lyophilized pellets were lysed in 9.2N valeric acid (2 mL/g of pellet), diluted to 2.3N acid with distilled and deionized water and stirred for 1 hour at room temperature. The cell lysate was clarified by centrifugation and applied to an SDS polyacrylamide gel for electrophoresis. FIG. 15 represents the polyacrylamide gel depicting this purification of ompF, a native *E. coli* structural protein from a lyophilized *E. coli* cell pellet. The ompF protein was than blotted onto a nitrocellulose membrane for N-terminal sequencing. The resulting 30 amino acids of N-terminal sequence led to the identification of *E. coli* outer membrane protein, ompF. This simple extraction procedure yielded a purity of approximately 85% based on coomassie-blue staining.

EXAMPLE 7

Organic Acid Extraction of Recognin B1 Protein

Figure 16:
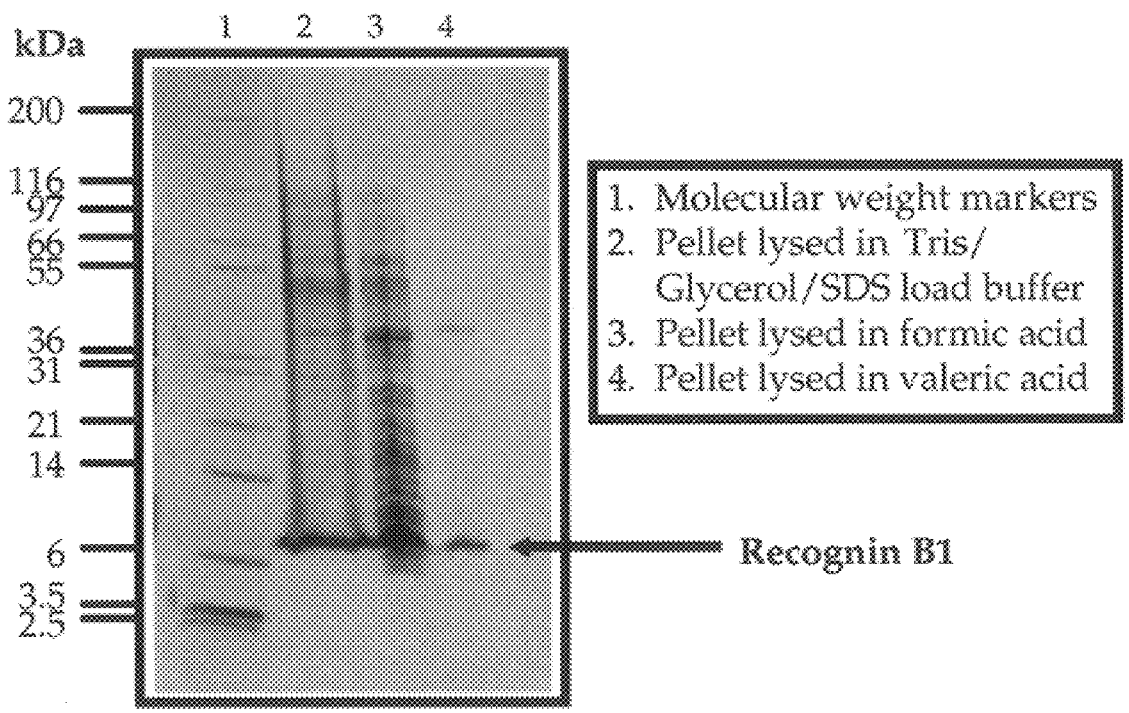
FIG. 16 presents a polyacrylamide gel of Recognin B1, a recombinant coiled coil structural protein. A cell pellet was lysed in either gel loading buffer, formic acid or valeric acid. Relative amounts of the cell pellet loaded onto the gel were 85, 400, 900 ug for the loading buffer, formic and valeric acid lysates, respectively. Acetic, propionic or butyric acids were unable to extract this protein.

In this example, the gene product of Recognin B1 (SEQ ID NO: 10), as set out in FIG. 10, was expressed as recombinant synthetic coiled protein Recognin B1 (SEQ ID NO: 11), as set out in FIG. 11, in *E.coli* (McGrath, K. P. and Kaplan, D. L. Mat. Res. Symp. Proc. 292, 83–91). The Recognin B1 gene was cloned into the expression vector pQE-9 (Qiagen) and transformed into the *E. coli* host cell, SG13009pREP4 (Qiagen). Cultures were grown to an $A_{600}$ of 1 in 4xYt medium (per liter: 32 g tryptone, 20 g yeast extract, 5 g NaCl) with ampicillin (400 ug/mL) and kanamycin (50 ug/mL). Expression was induced for two hours with 1 mM IPTG at which time the cells were harvested by centrifugation and stored for purification. Individual lyophilized pellets were lysed separately in 23N formic acid, 17.5N acetic acid, 13.4N propionic acid, 10.9N butyric acid or 9.2N valeric acid (2 mL/g of pellet), diluted to 2.3N acid with distilled and deionized water and stirred for 1 hour at room temperature. The cell lysates were clarified by centrifugation and analyzed by SDS-PAGE. FIG. 16 presents the polyacrylamide gel of Recognin B1, a recombinant coiled coil structural protein. A cell pellet was lysed in either gel loading buffer, formic acid or valeric acid. Relative amounts of the cell pellet loaded onto the gel were 85, 400, 900 ug for the loading buffer, formic and valeric acid lysates, respectively. Acetic, propionic or butyric acids were unable to extract this protein. The results indicated that formic and valeric acids were able to extract a significant quantity of Recognin B1 from *E. coli* pellets. The extracted protein did not appear to be degraded upon exposure to these organic acids. Of the two acids, valeric acid was able to extract Recognin B1 in a relatively pure form.

EXAMPLE 8

Processing and Fiber Spinning of Recombinant Silk Protein

Recombinant pETNcDS protein was purified as in Example 5, concentrated 100-fold by ultrafiltration and dialyzed into 10 mM $NaH_2PO_4$, 1 mM Tris, 20 mM NaCl, pH5 containing 1 M urea. The dialyzed sample was clarified by centrifugation and concentrated by ultrafiltration to a 25% (w/w) solution for fiber spinning. A Harvard Apparatus Infusion/Withdrawal Pump (Harvard Instruments, Natick MA) was used with a specialized microspinner (cavity volume 0.5 ml), and a 6 cm (0.005 I.D.) piece of tubing which was used as a spinneret. The silk solution was forced through the spinneret at a rate of 5–10 ul/min into a coagulation bath consisting of 90% methanol. Water insoluble fibers, 10–60 um in diameter, were produced and prepared for light microscopy (see FIG. 17).

EXAMPLE 9

Processing and Fiber Spinning the pET[(Sp1)$_4$/(Sp2)$_1$]$_4$ Recombinant Silk Protein pET[(SP1)$_4$/(SP2)$_1$]$_4$ (SEQ ID NO: 6) was purified as described in Example 4. The sample wasclarified by centrifugation and concentrated by ultrafiltration to 9.3% (w/w) solution for fiber spinning. A Harvard Apparatus Infusion/Withdrawal Pump (Harvard Instruments, Natick MA) was used with a specialized microspinner (cavity volume 0.5 ml) and a 6 cm (0.005 I.D.) piece of tubing which was used as a spinneret. The silk solution was forced through the spinneret at a rate of 2–5 ul/min into a coagulation bath consisting of 90% methanol. Fibers were produced from the solution. Fibers from the 9.3% solution were removed from the coagulation bath: said fibers were water insoluble and were subsequently prepared for light microscopy.

EXAMPLE 10

Figure 18:
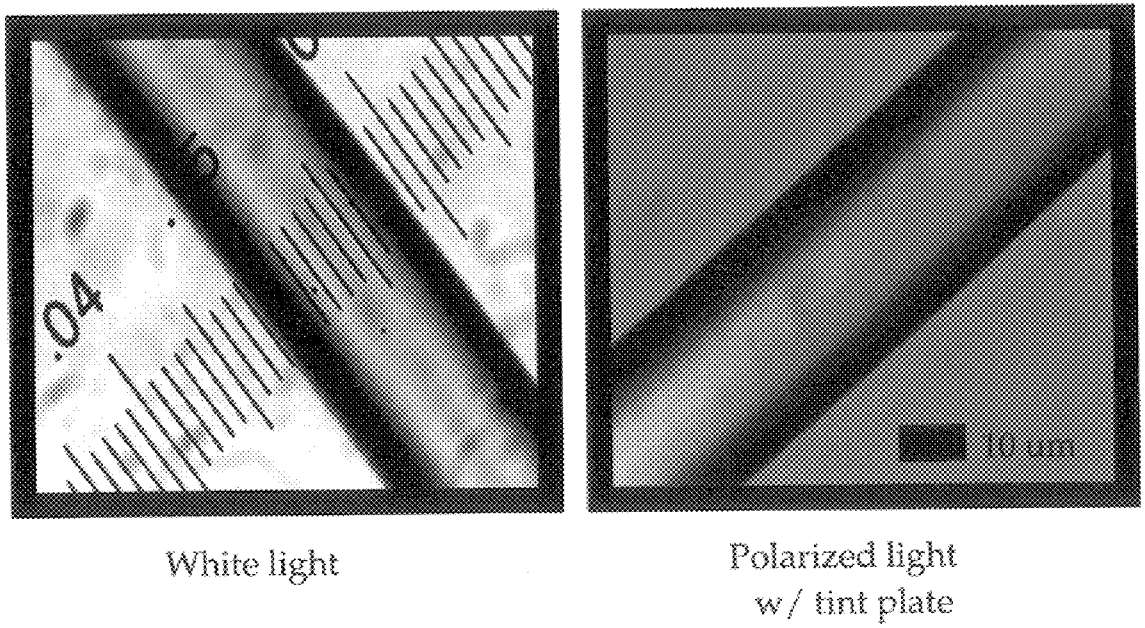
FIG. 18 presents photomicrographs of a fiber spun at a rate of 5 ul/min into a 90% methanol coagulation bath from a 12.5% aqueous solution of pQE[(Sp1)$_4$/(Sp2)$_1$]$_4$ viewed under a) white light and b) polarized light with a tint plate. The fibers present a consistent diameter of about 30 um.

Processing and Fiber Spinning the pQE[(Sp1)$_4$/(Sp2)$_1$]$_4$ Recombinant Silk Protein The pQE[(Sp1)$_4$/(Sp2)$_1$]$_4$ protein was purified by lysis in formic acid/guanidine hydrochloride as in Example 5 and dialyzed into 10 mM $NaH_2PO_4$, 1 mM Tris, 20 mM NaCl, pH 5 containing 160 mM urea. The dialyzed sample was clarified by centrifugation and concentrated by ultrafiltration to 6.5% and 12.5% (w/w) solution for fiber spinning. A Harvard Apparatus Infusion/Withdrawal Pump (Harvard Instruments, Natick MA) was used with a specialized microspinner (cavity volume 0.5 ml) and a 6 cm (0.005' I.D.) piece of tubing was used as a spinneret. The silk solution was forced through the spinneret at a rate of 5–10 ul/min into a coagulation bath consisting of 90% methanol. Fibers were produced from each solution. Only fibers from the 12.5% solution could be removed from the coagulation bath; they were water insoluble and prepared for light microscopy (see FIG. 18).

From the above description and examples, it should be clear that the present invention provides improved methods for purifying structural proteins and spinning spider silk proteins. Accordingly, this invention is not limited to the particular embodiments disclosed, but is intended to cover all modifications that are within the spirit and scope of the invention as defined by the appended claims.

We claim:

1. A method, comprising:
   (a) providing: i) a biological sample comprising one or more structural polypeptides; and ii) an acid consisting essentially of an organic acid;
   (b) treating said sample with said acid under conditions such that said one or more structural polypeptides are purified and recovered in a solution, said treating comprising mixing said sample with said acid, incubating said mixed sample and acid, and clarifying said mixed sample and acid to yield the recovered solution comprising said one or more purified polypeptides.

2. The method of claim 1, wherein said polypeptide is selected from SEQ ID NO: 2, SEQ ID NO: 4, SEQ ID NO: 6, SEQ ID NO: 8, SEQ ID NO: 9, and SEQ ID NO: 11.

3. The method of claim 1, wherein said biological sample comprises recombinant polypeptides.

4. The method of claim 1, wherein said biological sample comprises non-recombinant polypeptides.

5. The method of claim 1, wherein said acid is an organic acid.

6. The method of claim 5, wherein said organic acid is selected from formic, acetic, propionic, butyric, and valeric acids.

7. The method of claim 1, further comprising the steps of purifying the solution, concentrating the purified solution, and forcing the concentrated solution through a spinneret under conditions wherein insoluble fibers of polypeptides are produced.

8. A method, comprising:
   (a) providing: i) host cells expressing one or more recombinant structural polypeptides, and ii) a solution consisting essentially of an organic acid; and
   (b) treating said host cells with said solution to create a mixture of soluble and insoluble material, whereby said treating comprises mixing said cells with said acid, incubating said mixed cells and acid, and clarifying said mixed cells and acid to yield a recovered solution, said recovered solution comprising one or more purified polypeptides.

9. The method of claim 8, wherein said one or more polypeptides is selected from SEQ ID NO: 2, SEQ ID NO: 4, SEQ ID NO: 6, SEQ ID NO: 8, SEQ ID NO: 9, and SEQ ID NO: 11.

10. The method of claim 8, wherein said organic acid is selected from formic acid, acetic acid, propionic acid, butyric acid, and valeric acid.

11. The method of claim 8, further comprising purifying the solution, concentrating the purified solution, and forcing the concentrated solution through a spinneret under conditions wherein insoluble fibers of polypeptides are produced.

12. A method, comprising:
    (a) providing: i) bacterial cells expressing one or more recombinant structural polypeptides, and ii) a solution consisting essentially of an organic acid selected from formic acid, acetic acid, propionic acid, butyric acid, and valeric acid; and
    (b) treating said bacterial cells with said solution to create a mixture of soluble and insoluble material, whereby said treating comprises mixing said cells with said acid, incubating said mixed cells and acid, and clarifying said mixed cells and acid to yield a recovered solution, said recovered solution comprising one or more purified polypeptides.

13. The method of claim 12, wherein said one or more polypeptides is selected from SEQ ID NO: 2, SEQ ID NO: 4, SEQ ID NO: 6, SEQ ID NO: 8, and SEQ ID NO: 11.

14. The method of claim 12, further comprising the steps of purifying the solution, concentrating said recovered one or more recombinant polypeptides to create a concentrated purified solution, and forcing said concentrated solution through a spinneret under conditions wherein insoluble fibers of polypeptides are produced.

* * * * *

SEQUENCE LISTING

<160> NUMBER OF SEQ ID NOS: 11

<210> SEQ ID NO 1
<211> LENGTH: 876
<212> TYPE: DNA
<213> ORGANISM: Nephila clavipes

<400> SEQUENCE: 1

```
atgagaggat cgcatcacca tcaccatcac ggatccatgg ctagcggtag aggcgggctg      60
ggtggccagg gtgcaggtgc ggctgcggct gccgcggcag cggccgcagg cggtgccggc     120
```

-continued

```
caaggtggct atggcggcct gggttctcag gggactagcg gtagaggcgg gctgggtggc    180
cagggtgcag gtgcggctgc ggctgccgcg gcagcggccg caggcggtgc cggccaaggt    240
ggctatggcg gcctgggttc tcaggggact agcggtagag gcgggctggg tggccagggt    300
gcaggtgcgg ctgcggctgc cgcggcagcg gccgcaggcg gtgccggcca aggtggctat    360
ggcggcctgg gttctcaggg gactagcggt agaggcgggc tgggtggcca gggtgcaggt    420
gcggctgcgg ctgccgcggc agcggccgca ggcggtgccg gccaaggtgg ctatggcggc    480
ctgggttctc aggggactag cggtagaggc gggctgggtg gccagggtgc aggtgcggct    540
gcggctgccg cggcagcggc cgcaggcggt gccggccaag gtggctatgg cggcctgggt    600
tctcagggga ctagcggtag aggcgggctg gtggccagg gtgcaggtgc ggctgcggct    660
gccgcggcag cggccgcagg cggtgccggc caaggyggct atggcggcct gggttctcag    720
gggactagcg gtagaggcgg gctgggtggc cagggtgcag gtgcggctgc ggctgccgcg    780
gcagcggccg caggcggtgc cggccaaggt ggctatggcg gcctgggttc tcaggggact    840
agtgggatcc gtcgacctgc agccaagctt aattag                              876
```

<210> SEQ ID NO 2
<211> LENGTH: 291
<212> TYPE: PRT
<213> ORGANISM: Nephila clavipes

<400> SEQUENCE: 2

```
Met Arg Gly Ser His His His His His His Gly Ser Met Ala Ser Gly
  1               5                  10                  15

Arg Gly Gly Leu Gly Gly Gln Gly Ala Gly Ala Ala Ala Ala Ala Ala
             20                  25                  30

Ala Ala Ala Ala Gly Gly Ala Gly Gln Gly Gly Tyr Gly Gly Leu Gly
         35                  40                  45

Ser Gln Gly Thr Ser Gly Arg Gly Gly Leu Gly Gly Gln Gly Ala Gly
     50                  55                  60

Ala Ala Ala Ala Ala Ala Ala Ala Ala Gly Gly Ala Gly Gln Gly
 65                  70                  75                  80

Gly Tyr Gly Gly Leu Gly Ser Gln Gly Thr Ser Gly Arg Gly Gly Leu
                 85                  90                  95

Gly Gly Gln Gly Ala Gly Ala Ala Ala Ala Ala Ala Ala Ala Ala Ala
            100                 105                 110

Gly Gly Ala Gly Gln Gly Gly Tyr Gly Gly Leu Gly Ser Gln Gly Thr
        115                 120                 125

Ser Gly Arg Gly Gly Leu Gly Gly Gln Gly Ala Gly Ala Ala Ala Ala
    130                 135                 140

Ala Ala Ala Ala Ala Ala Gly Gly Ala Gly Gln Gly Gly Tyr Gly Gly
145                 150                 155                 160

Leu Gly Ser Gln Gly Thr Ser Gly Arg Gly Gly Leu Gly Gly Gln Gly
                165                 170                 175

Ala Gly Ala Ala Ala Ala Ala Ala Ala Ala Ala Gly Gly Ala Gly
            180                 185                 190

Gln Gly Gly Tyr Gly Gly Leu Gly Ser Gln Gly Thr Ser Gly Arg Gly
        195                 200                 205

Gly Leu Gly Gly Gln Gly Ala Gly Ala Ala Ala Ala Ala Ala Ala Ala
    210                 215                 220

Ala Ala Gly Gly Ala Gly Gln Gly Gly Tyr Gly Gly Leu Gly Ser Gln
225                 230                 235                 240
```

-continued

```
Gly Thr Ser Gly Arg Gly Gly Leu Gly Gly Gln Gly Ala Gly Ala Ala
                245                 250                 255
Ala Ala Ala Ala Ala Ala Ala Gly Gly Ala Gly Gln Gly Tyr
            260                 265                 270
Gly Gly Leu Gly Ser Gln Gly Thr Ser Gly Ile Arg Arg Pro Ala Ala
        275                 280                 285
Lys Leu Asn
    290

<210> SEQ ID NO 3
<211> LENGTH: 2046
<212> TYPE: DNA
<213> ORGANISM: Nephila clavipes

<400> SEQUENCE: 3
atgagaggat cgcatcacca tcaccatcac ggatccatgg ctagcggtag aggcgggctg      60
ggtggccagg gtgcaggtgc ggctgcggct gccgcggcag cggccgcagg cggtgccggc     120
caaggtggct atgcggcct  gggttctcag gggactagcg gtagaggcgg gctgggtggc     180
cagggtgcag gtgcggctgc ggctgccgcg gcagcggccg caggcggtgc cggccaaggt     240
ggctatggcg gcctgggttc tcaggggact agcggtagag gcgggctggg tggccagggt     300
gcaggtgcgc tgcggctgc  cgcggcagcg gccgcaggcg gtgccggcca aggtggctat     360
ggcggcctgg gttctcaggg gactagcggt agaggcgggc tgggtggcca gggtgcaggt     420
gcggctgcgc tgccgcggc  agcggccgca ggcggtgccg gccaaggtgg ctatggcggc     480
ctgggttctc aggggactag cggtccgggc ggttatggtc cgggtcaaca actagcggt      540
agaggcgggc tgggtggcca gggtgcaggt gcggctgcgg ctgccgcggc agcggccgca     600
ggcggtgccg gccaaggtgg ctatggcggc ctgggttctc aggggactag cggtagaggc     660
gggctgggtg gccagggtgc aggtgcggct gcggctgccg cggcagcggc cgcaggcggt     720
gccggccaag gtggctatgg cggcctgggt tctcagggga ctagcggtag aggcgggctg     780
ggtggccagg gtgcaggtgc ggctgcggct gccgcggcag cggccgcagg cggtgccggc     840
caaggtggct atgcggcct  gggttctcag gggactagcg gtagaggcgg gctgggtggc     900
cagggtgcag gtgcggctgc ggctgccgcg gcagcggccg caggcggtgc cggccaaggt     960
ggctatggcg gcctgggttc tcaggggact agcggtccgg gcggttatgg tccgggtcaa    1020
caaactagcg gtagaggcgg gctgggtggc cagggtgcag gtgcggctgc ggctgccgcg    1080
gcagcggccg caggcggtgc cggccaaggt ggctatggcg gcctgggttc tcaggggact    1140
agcggtagag gcgggctggg tggccagggt gcaggtgcgg ctgcggctgc cgcggcagcg    1200
gccgcaggcg gtgccggcca aggtggctat ggcggcctgg gttctcaggg gactagcggt    1260
agaggcgggc tgggtggcca gggtgcaggt gcggctgcgg ctgccgcggc agcggccgca    1320
ggcggtgccg gccaaggtgg ctatggcggc ctgggttctc aggggactag cggtagaggc    1380
gggctgggtg gccagggtgc aggtgcggct gcggctgccg cggcagcggc cgcaggcggt    1440
gccggccaag gtggctatgg cggcctgggt tctcagggga ctagcggtcc gggcggttat    1500
ggtccgggtc aacaaactag cggtagaggc gggctgggtg gccagggtgc aggtgcggct    1560
gcggctgccg cggcagcggc cgcaggcggt gccggccaag gtggctatgg cggcctgggt    1620
tctcagggga ctagcggtag aggcgggctg ggtggccagg gtgcaggtgc ggctgcggct    1680
gccgcggcag cggccgcagg cggtgccggc caaggtggct atgcggcct  gggttctcag    1740
gggactagcg gtagaggcgg gctgggtggc cagggtgcag gtgcggctgc ggctgccgcg    1800
```

-continued

```
gcagcggccg caggcggtgc cggccaaggt ggctatggcg gcctgggttc tcagggcact    1860
agcggtagag gcgggctggg tggccagggt gcaggtgcgg ctgcggctgc cgcggcagcg    1920
gccgcaggcg gtgccggcca aggtggctat ggcggcctgg gttctcaggg gactagcggt    1980
ccgggcggtt atggtccggg tcaacaaact agtgggatcc gtcgacctgc agccaagctt    2040
aattag                                                              2046
```

<210> SEQ ID NO 4
<211> LENGTH: 681
<212> TYPE: PRT
<213> ORGANISM: Nephila clavipes

<400> SEQUENCE: 4

```
Met Arg Gly Ser His His His His His His Gly Ser Met Ala Ser Gly
  1               5                  10                  15

Arg Gly Gly Leu Gly Gly Gln Gly Ala Gly Ala Ala Ala Ala Ala Ala
             20                  25                  30

Ala Ala Ala Ala Gly Gly Ala Gly Gln Gly Gly Tyr Gly Gly Leu Gly
         35                  40                  45

Ser Gln Gly Thr Ser Gly Arg Gly Gly Leu Gly Gly Gln Gly Ala Gly
     50                  55                  60

Ala Ala Ala Ala Ala Ala Ala Ala Gly Gly Ala Gly Gln Gly
 65                  70                  75                  80

Gly Tyr Gly Gly Leu Gly Ser Gln Gly Thr Ser Gly Arg Gly Gly Leu
                 85                  90                  95

Gly Gly Gln Gly Ala Gly Ala Ala Ala Ala Ala Ala Ala Ala
            100                 105                 110

Gly Gly Ala Gly Gln Gly Gly Tyr Gly Gly Leu Gly Ser Gln Gly Thr
        115                 120                 125

Ser Gly Arg Gly Gly Leu Gly Gly Gln Gly Ala Gly Ala Ala Ala Ala
    130                 135                 140

Ala Ala Ala Ala Ala Ala Gly Gly Ala Gly Gln Gly Gly Tyr Gly Gly
145                 150                 155                 160

Leu Gly Ser Gln Gly Thr Ser Gly Pro Gly Gly Tyr Gly Pro Gly Gln
                165                 170                 175

Gln Thr Ser Gly Arg Gly Gly Leu Gly Gly Gln Gly Ala Gly Ala Ala
            180                 185                 190

Ala Ala Ala Ala Ala Ala Ala Gly Gly Ala Gly Gln Gly Gly Tyr
        195                 200                 205

Gly Gly Leu Gly Ser Gln Gly Thr Ser Gly Arg Gly Gly Leu Gly Gly
    210                 215                 220

Gln Gly Ala Gly Ala Ala Ala Ala Ala Ala Ala Ala Ala Gly Gly
225                 230                 235                 240

Ala Gly Gln Gly Gly Tyr Gly Gly Leu Gly Ser Gln Gly Thr Ser Gly
                245                 250                 255

Arg Gly Gly Leu Gly Gly Gln Gly Ala Gly Ala Ala Ala Ala Ala
            260                 265                 270

Ala Ala Ala Ala Gly Gly Ala Gly Gln Gly Gly Tyr Gly Gly Leu Gly
        275                 280                 285

Ser Gln Gly Thr Ser Gly Arg Gly Gly Leu Gly Gly Gln Gly Ala Gly
    290                 295                 300

Ala Ala Ala Ala Ala Ala Ala Ala Ala Gly Gly Ala Gly Gln Gly
305                 310                 315                 320
```

Gly Tyr Gly Gly Leu Gly Ser Gln Gly Thr Ser Gly Pro Gly Gly Tyr
                325                 330                 335

Gly Pro Gly Gln Gln Thr Ser Gly Arg Gly Gly Leu Gly Gly Gln Gly
            340                 345                 350

Ala Gly Ala Ala Ala Ala Ala Ala Ala Ala Ala Ala Ala Gly Gly Ala Gly
            355                 360                 365

Gln Gly Gly Tyr Gly Gly Leu Gly Ser Gln Gly Thr Ser Gly Arg Gly
    370                 375                 380

Gly Leu Gly Gly Gln Gly Ala Gly Ala Ala Ala Ala Ala Ala Ala Ala
385                 390                 395                 400

Ala Ala Gly Gly Ala Gly Gln Gly Gly Tyr Gly Gly Leu Gly Ser Gln
                405                 410                 415

Gly Thr Ser Gly Arg Gly Gly Leu Gly Gly Gln Gly Ala Gly Ala Ala
                420                 425                 430

Ala Ala Ala Ala Ala Ala Ala Gly Gly Ala Gly Gln Gly Gly Tyr
            435                 440                 445

Gly Gly Leu Gly Ser Gln Gly Thr Ser Gly Arg Gly Gly Leu Gly Gly
    450                 455                 460

Gln Gly Ala Gly Ala Ala Ala Ala Ala Ala Ala Ala Ala Gly Gly
465                 470                 475                 480

Ala Gly Gln Gly Gly Tyr Gly Gly Leu Gly Ser Gln Gly Thr Ser Gly
            485                 490                 495

Pro Gly Gly Tyr Gly Pro Gly Gln Gln Thr Ser Gly Arg Gly Gly Leu
            500                 505                 510

Gly Gly Gln Gly Ala Gly Ala Ala Ala Ala Ala Ala Ala Ala Ala
            515                 520                 525

Gly Gly Ala Gly Gln Gly Gly Tyr Gly Gly Leu Gly Ser Gln Gly Thr
    530                 535                 540

Ser Gly Arg Gly Gly Leu Gly Gly Gln Gly Ala Gly Ala Ala Ala Ala
545                 550                 555                 560

Ala Ala Ala Ala Ala Ala Gly Gly Ala Gly Gln Gly Gly Tyr Gly Gly
                565                 570                 575

Leu Gly Ser Gln Gly Thr Ser Gly Arg Gly Gly Leu Gly Gly Gln Gly
            580                 585                 590

Ala Gly Ala Ala Ala Ala Ala Ala Ala Ala Ala Ala Gly Gly Ala Gly
    595                 600                 605

Gln Gly Gly Tyr Gly Gly Leu Gly Ser Gln Gly Thr Ser Gly Arg Gly
    610                 615                 620

Gly Leu Gly Gly Gln Gly Ala Gly Ala Ala Ala Ala Ala Ala Ala Ala
625                 630                 635                 640

Ala Ala Gly Gly Ala Gly Gln Gly Gly Tyr Gly Gly Leu Gly Ser Gln
                645                 650                 655

Gly Thr Ser Gly Pro Gly Gly Tyr Gly Pro Gly Gln Gln Thr Ser Gly
            660                 665                 670

Ile Arg Arg Pro Ala Ala Lys Leu Asn
            675                 680

<210> SEQ ID NO 5
<211> LENGTH: 2076
<212> TYPE: DNA
<213> ORGANISM: Nephila clavipes

<400> SEQUENCE: 5
atggctagca tgactggtgg acagcaaatg ggtcgcggat ccatggctag cggtagaggc    60

-continued

| | |
|---|---|
| gggctgggtg gccagggtgc aggtgcggct gcggctgccg cggcagcggc cgcaggcggt | 120 |
| gccggccaag gtggctatgg cggcctgggt tctcagggga ctagcggtag aggcgggctg | 180 |
| ggtggccagg gtgcaggtgc ggctgcggct gccgcggcag cggccgcagg cggtgccggc | 240 |
| caaggtggct atggcggcct gggttctcag gggactagcg gtagaggcgg gctgggtggc | 300 |
| cagggtgcag gtgcggctgc ggctgccgcg gcagcggccg caggcggtgc cggccaaggt | 360 |
| ggctatggcg gcctgggttc tcaggggact agcggtagag gcgggctggg tggccagggt | 420 |
| gcaggtgcgg ctgcggctgc cgcggcagcg gccgcaggcg gtgccggcca aggtggctat | 480 |
| ggcggcctgg gttctcaggg gactagcggt ccgggcggtt atggtccggg tcaacaaact | 540 |
| agcggtagag gcgggctggg tggccagggt gcaggtgcgg ctgcggctgc cgcggcagcg | 600 |
| gccgcaggcg gtgccggcca agtggctat ggcggcctgg gttctcaggg gactagcggt | 660 |
| agaggcgggc tgggtggcca gggtgcaggt gcggctgcgg ctgccgcggc agcggccgca | 720 |
| ggcggtgccg gccaaggtgg ctatggcggc ctgggttctc aggggactag cggtagaggc | 780 |
| gggctgggtg gccagggtgc aggtgcggct gcggctgccg cggcagcggc cgcaggcggt | 840 |
| gccggccaag gtggctatgg cggcctgggt tctcagggga ctagcggtag aggcgggctg | 900 |
| ggtggccagg gtgcaggtgc ggctgcggct gccgcggcag cggccgcagg cggtgccggc | 960 |
| caaggtggct atggcggcct gggttctcag gggactagcg gtccgggcgg ttatggtccg | 1020 |
| ggtcaacaaa ctagcggtag aggcgggctg gtggccagg gtgcaggtgc ggctgcggct | 1080 |
| gccgcggcag cggccgcagg cggtgccggc caaggtggct atgcggcct gggttctcag | 1140 |
| gggactagcg gtagaggcgg gctgggtggc cagggtgcag gtgcggctgc ggctgccgcg | 1200 |
| gcagcggccg caggcggtgc cggccaaggt ggctatggcg gcctgggttc tcaggggact | 1260 |
| agcggtagag gcgggctggg tggccagggt gcaggtgcgg ctgcggctgc cgcggcagcg | 1320 |
| gccgcaggcg gtgccggcca agtggctat ggcggcctgg gttctcaggg gactagcggt | 1380 |
| agaggcgggc tgggtggcca gggtgcaggt gcggctgcgg ctgccgcggc agcggccgca | 1440 |
| ggcggtgccg gccaaggtgg ctatggcggc ctgggttctc aggggactag cggtccgggc | 1500 |
| ggttatggtc cgggtcaaca aactagcggt agaggcgggc tgggtggcca gggtgcaggt | 1560 |
| gcggctgcgg ctgccgcggc agcggccgca ggcggtgccg gccaaggtgg ctatggcggc | 1620 |
| ctgggttctc aggggactag cggtagaggc gggctgggtg gccagggtgc aggtgcggct | 1680 |
| gcggctgccg cggcagcggc cgcaggcggt gccggccaag gtggctatgg cggcctgggt | 1740 |
| tctcagggga ctagcggtag aggcgggctg gtggccagg gtgcaggtgc ggctgcggct | 1800 |
| gccgcggcag cggccgcagg cggtgccggc caaggtggct atggcggcct gggttctcag | 1860 |
| gggactagcg gtagaggcgg gctgggtggc cagggtgcag gtgcggctgc ggctgccgcg | 1920 |
| gcagcggccg caggcggtgc cggccaaggt ggctatggcg gcctgggttc tcaggggact | 1980 |
| agcggtccgg gcggttatgg tccgggtcaa caaactagtg gatccgaat tcgagctccg | 2040 |
| tcgacaagct tcgagcacca ccaccaccac cactga | 2076 |

<210> SEQ ID NO 6
<211> LENGTH: 691
<212> TYPE: PRT
<213> ORGANISM: Nephila clavipes

<400> SEQUENCE: 6

Met Ala Ser Met Thr Gly Gly Gln Gln Met Gly Arg Gly Ser Met Ala
 1               5                  10                  15

-continued

```
Ser Gly Arg Gly Gly Leu Gly Gly Gln Gly Ala Gly Ala Ala Ala
         20                  25                  30
Ala Ala Ala Ala Ala Ala Gly Gly Ala Gly Gln Gly Gly Tyr Gly Gly
         35                  40                  45
Leu Gly Ser Gln Gly Thr Ser Gly Arg Gly Gly Leu Gly Gly Gln Gly
         50                  55                  60
Ala Gly Ala Ala Ala Ala Ala Ala Ala Ala Ala Ala Gly Gly Ala Gly
 65                  70                  75                  80
Gln Gly Gly Tyr Gly Gly Leu Gly Ser Gln Gly Thr Ser Gly Arg Gly
                 85                  90                  95
Gly Leu Gly Gly Gln Gly Ala Gly Ala Ala Ala Ala Ala Ala Ala
                100                 105                 110
Ala Ala Gly Gly Ala Gly Gln Gly Gly Tyr Gly Gly Leu Gly Ser Gln
        115                 120                 125
Gly Thr Ser Gly Arg Gly Gly Leu Gly Gly Gln Gly Ala Gly Ala Ala
        130                 135                 140
Ala Ala Ala Ala Ala Ala Ala Gly Gly Ala Gly Gln Gly Gly Tyr
145                 150                 155                 160
Gly Gly Leu Gly Ser Gln Gly Thr Ser Gly Pro Gly Gly Tyr Gly Pro
                165                 170                 175
Gly Gln Gln Thr Ser Gly Arg Gly Gly Leu Gly Gly Gln Gly Ala Gly
                180                 185                 190
Ala Ala Ala Ala Ala Ala Ala Ala Ala Gly Gly Ala Gly Gln Gly
        195                 200                 205
Gly Tyr Gly Gly Leu Gly Ser Gln Gly Thr Ser Gly Arg Gly Gly Leu
    210                 215                 220
Gly Gly Gln Gly Ala Gly Ala Ala Ala Ala Ala Ala Ala Ala Ala
225                 230                 235                 240
Gly Gly Ala Gly Gln Gly Gly Tyr Gly Gly Leu Gly Ser Gln Gly Thr
                245                 250                 255
Ser Gly Arg Gly Gly Leu Gly Gly Gln Gly Ala Gly Ala Ala Ala Ala
                260                 265                 270
Ala Ala Ala Ala Ala Ala Gly Gly Ala Gly Gln Gly Gly Tyr Gly Gly
        275                 280                 285
Leu Gly Ser Gln Gly Thr Ser Gly Arg Gly Gly Leu Gly Gly Gln Gly
        290                 295                 300
Ala Gly Ala Ala Ala Ala Ala Ala Ala Ala Ala Gly Gly Ala Gly
305                 310                 315                 320
Gln Gly Gly Tyr Gly Gly Leu Gly Ser Gln Gly Thr Ser Gly Pro Gly
                325                 330                 335
Gly Tyr Gly Pro Gly Gln Gln Thr Ser Gly Arg Gly Gly Leu Gly Gly
                340                 345                 350
Gln Gly Ala Gly Ala Ala Ala Ala Ala Ala Ala Ala Ala Gly Gly
        355                 360                 365
Ala Gly Gln Gly Gly Tyr Gly Gly Leu Gly Ser Gln Gly Thr Ser Gly
        370                 375                 380
Arg Gly Gly Leu Gly Gly Gln Gly Ala Gly Ala Ala Ala Ala Ala Ala
385                 390                 395                 400
Ala Ala Ala Ala Gly Gly Ala Gly Gln Gly Gly Tyr Gly Gly Leu Gly
                405                 410                 415
Ser Gln Gly Thr Ser Gly Arg Gly Gly Leu Gly Gly Gln Gly Ala Gly
                420                 425                 430
Ala Ala Ala Ala Ala Ala Ala Ala Ala Ala Gly Gly Ala Gly Gln Gly
```

```
             435                 440                  445
Gly Tyr Gly Gly Leu Gly Ser Gln Gly Thr Ser Gly Arg Gly Gly Leu
            450                 455                 460
Gly Gly Gln Gly Ala Gly Ala Ala Ala Ala Ala Ala Ala Ala Ala Ala
465                 470                 475                 480
Gly Gly Ala Gly Gln Gly Gly Tyr Gly Gly Leu Gly Ser Gln Gly Thr
                485                 490                 495
Ser Gly Pro Gly Gly Tyr Gly Pro Gly Gln Gln Thr Ser Gly Arg Gly
            500                 505                 510
Gly Leu Gly Gly Gln Gly Ala Gly Ala Ala Ala Ala Ala Ala Ala Ala
            515                 520                 525
Ala Ala Gly Gly Ala Gly Gln Gly Gly Tyr Gly Gly Leu Gly Ser Gln
530                 535                 540
Gly Thr Ser Gly Arg Gly Gly Leu Gly Gly Gln Gly Ala Gly Ala Ala
545                 550                 555                 560
Ala Ala Ala Ala Ala Ala Ala Gly Gly Ala Gly Gln Gly Gly Tyr
                565                 570                 575
Gly Gly Leu Gly Ser Gln Gly Thr Ser Gly Arg Gly Gly Leu Gly Gly
                580                 585                 590
Gln Gly Ala Gly Ala Ala Ala Ala Ala Ala Ala Ala Ala Gly Gly
            595                 600                 605
Ala Gly Gln Gly Gly Tyr Gly Gly Leu Gly Ser Gln Gly Thr Ser Gly
610                 615                 620
Arg Gly Gly Leu Gly Gly Gln Gly Ala Gly Ala Ala Ala Ala Ala
625                 630                 635                 640
Ala Ala Ala Ala Gly Gly Ala Gly Gln Gly Gly Tyr Gly Gly Leu Gly
                645                 650                 655
Ser Gln Gly Thr Ser Gly Pro Gly Gly Tyr Gly Pro Gly Gln Gln Thr
            660                 665                 670
Ser Gly Ile Arg Ile Arg Ala Pro Ser Thr Ser Phe Glu His His His
        675                 680                 685
His His His
    690

<210> SEQ ID NO 7
<211> LENGTH: 1588
<212> TYPE: DNA
<213> ORGANISM: Nephila clavipes

<400> SEQUENCE: 7
atggctagca tgactggtgg acagcaaatg ggtcggatcc gaattcgtgg atatggaggt      60
cttggtggac aaggtgccgg acaaggagct ggtgcagccg ccgcagcagc agctggtggt     120
gccggacaag gaggatatgg aggtcttgga agccaaggtg ctggacgagg tggacaaggt     180
gcaggcgcag ccgcagccgc agctggaggt gctggtcaag gaggatacgg aggtcttgga     240
agccaaggtg ctggacgagg aggattaggt ggacaaggtg caggtgcagc agcagcagct     300
ggaggtgtcg gacaaggagg actaggtgga caaggtgctg gacaaggagc tggagcagct     360
gctgcagcag ctggtggtgc cggacaagga ggatatggag gtctcggaag ccaaggtgca     420
ggacgaggtg gatcaggtgg acaagggca ggtgcagcag cagcagcagc tggaggtgcc     480
ggacaaggag gatatggagg tcttggaagc caaggtgcag gacgaggtgg attaggtgga     540
cagggtgcag gtgcagcagc agcagcagca gccggaggtg ctggacaagg aggatacggt     600
ggtcttggtg gacaaggtgc cggacaaggt ggctatggag gacttggaag ccaaggtgct     660
```

-continued

```
ggacgaggag gattaggtgg acaaggtgca ggtgcagcag cagcagctgg aggtgccgga    720
caaggaggac taggtggaca aggagctgga gcagccgctg cagcagctgg tggtgccgga    780
caaggaggat atggaggtct tggaagccaa ggtgctggac gaggtggaca aggtgcaggc    840
gcagccgcag cagcagccgg aggtgctgga caaggaggat acggtggaca aggtgccgga    900
caaggaggct atggaggact tggaagccaa ggtgctggac gaggaggatt aggtggacaa    960
ggtgcaggtg cagcagcagc agcagcagca gctggaggtg ccggacaagg aggattaggt   1020
ggacaaggtg caggtgcagc agcagcagca gctggaggtc tggacaagg aggattaggt    1080 ggacaaggtg ctggacaagg agctggagca gccgctgcag cagccgctgc agcagctggt   1140
ggtgttagac aaggaggata tggaggtctt ggaagccaag gtgctggacg aggtggacaa   1200
ggtgcaggcg cagccgcagc agcagccgga ggtgctggac aaggaggata tggtggtctt   1260
ggtggacaag gtgttggacg aggtggatta ggtggacaag gtgcaggcgc agcggcagct   1320
gttggtgctg gacaaggagg atatggtggt gttggttctg ggcgtctgc tgcctctgca    1380 gctgcatccc gtttgtcttc tcctcaagct agttcaagag tttcatcagc tgtttccaac   1440
ttggttgcaa gtggtcctac taattctgcg gccttgtcaa gtacaatcag taatgtggtt   1500
tcacaaatag gcgccagcaa tcctggtctt tctggatgtg atgtcctcat tcaagctctt   1560
ctcgagcacc accaccacca ccactgaa                                     1588
```

<210> SEQ ID NO 8
<211> LENGTH: 528
<212> TYPE: PRT
<213> ORGANISM: Nephila clavipes

<400> SEQUENCE: 8

```
Met Ala Ser Met Thr Gly Gly Gln Gln Met Gly Arg Ile Arg Ile Arg
  1               5                  10                  15
Gly Tyr Gly Gly Leu Gly Gly Gln Gly Ala Gly Gln Gly Ala Gly Ala
             20                  25                  30
Ala Ala Ala Ala Ala Ala Gly Gly Ala Gly Gln Gly Gly Tyr Gly Gly
         35                  40                  45
Leu Gly Ser Gln Gly Ala Gly Arg Gly Gly Gln Gly Ala Gly Ala Ala
     50                  55                  60
Ala Ala Ala Ala Gly Gly Ala Gly Gln Gly Gly Tyr Gly Gly Leu Gly
 65                  70                  75                  80
Ser Gln Gly Ala Gly Arg Gly Gly Leu Gly Gly Gln Gly Ala Gly Ala
                 85                  90                  95
Ala Ala Ala Gly Gly Val Gly Gln Gly Gly Leu Gly Gly Gln Gly
            100                 105                 110
Ala Gly Gln Gly Ala Gly Ala Ala Ala Ala Ala Gly Gly Ala Gly
        115                 120                 125
Gln Gly Gly Tyr Gly Gly Leu Gly Ser Gln Gly Ala Gly Arg Gly Gly
    130                 135                 140
Ser Gly Gly Gln Gly Ala Gly Ala Ala Ala Ala Ala Gly Gly Ala
145                 150                 155                 160
Gly Gln Gly Gly Tyr Gly Gly Leu Gly Ser Gln Gly Ala Gly Arg Gly
                165                 170                 175
Gly Leu Gly Gly Gln Gly Ala Gly Ala Ala Ala Ala Ala Ala Gly
            180                 185                 190
Gly Ala Gly Gln Gly Gly Tyr Gly Gly Leu Gly Gly Gln Gly Ala Gly
        195                 200                 205
```

-continued

```
Gln Gly Gly Tyr Gly Gly Leu Gly Ser Gln Gly Ala Gly Arg Gly Gly
        210                 215                 220
Leu Gly Gly Gln Gly Ala Gly Ala Ala Ala Ala Gly Gly Ala Gly
225                 230                 235                 240
Gln Gly Gly Leu Gly Gly Gln Gly Ala Gly Ala Ala Ala Ala Ala
            245                 250                 255
Gly Gly Ala Gly Gln Gly Gly Tyr Gly Gly Leu Gly Ser Gln Gly Ala
                260                 265                 270
Gly Arg Gly Gly Gln Gly Ala Gly Ala Ala Ala Ala Ala Gly Gly
        275                 280                 285
Ala Gly Gln Gly Gly Tyr Gly Gly Gln Gly Ala Gly Gln Gly Gly Tyr
    290                 295                 300
Gly Gly Leu Gly Ser Gln Gly Ala Gly Arg Gly Gly Leu Gly Gly Gln
305                 310                 315                 320
Gly Ala Gly Ala Ala Ala Ala Ala Ala Gly Gly Ala Gly Gln
            325                 330                 335
Gly Gly Leu Gly Gly Gln Gly Ala Gly Ala Ala Ala Ala Ala Gly
        340                 345                 350
Gly Ala Gly Gln Gly Gly Leu Gly Gly Gln Gly Ala Gly Gln Gly Ala
    355                 360                 365
Gly Ala Ala Ala Ala Ala Ala Ala Ala Gly Gly Val Arg Gln
370                 375                 380
Gly Gly Tyr Gly Gly Leu Gly Ser Gln Gly Ala Gly Arg Gly Gly Gln
385                 390                 395                 400
Gly Ala Gly Ala Ala Ala Ala Gly Gly Ala Gly Gln Gly Gly
            405                 410                 415
Thr Gly Gly Leu Gly Gly Gln Gly Val Gly Ala Gly Gly Leu Gly Gly
                420                 425                 430
Gln Gly Ala Gly Ala Ala Ala Val Gly Ala Gly Gln Gly Gly Tyr
        435                 440                 445
Gly Gly Val Gly Ser Gly Ala Ser Ala Ala Ser Ala Ala Ala Ser Arg
    450                 455                 460
Leu Ser Ser Pro Gln Ala Ser Ser Arg Val Ser Ser Ala Val Ser Asn
465                 470                 475                 480
Leu Val Ala Ser Gly Pro Thr Asn Ser Ala Ala Leu Ser Ser Thr Ile
            485                 490                 495
Ser Asn Val Val Ser Gln Ile Gly Ala Ser Asn Pro Gly Leu Ser Gly
                500                 505                 510
Cys Asp Val Leu Ile Gln Ala Leu Leu Gly His His His His His
            515                 520                 525
```

<210> SEQ ID NO 9
<211> LENGTH: 341
<212> TYPE: PRT
<213> ORGANISM: Nephila clavipes

<400> SEQUENCE: 9

```
Ala Glu Ile Tyr Asn Lys Asp Gly Asn Lys Val Asp Leu Tyr Gly Lys
 1               5                  10                  15
Ala Val Gly Leu His Tyr Phe Ser Lys Gly Asn Gly Glu Asn Ser Tyr
            20                  25                  30
Gly Gly Asn Gly Asp Met Thr Tyr Ala Arg Leu Gly Phe Lys Gly Glu
        35                  40                  45
Thr Gln Ile Asn Ser Asp Leu Thr Gly Tyr Gly Gln Trp Glu Tyr Asn
```

```
              50                  55                  60
Phe Gln Gly Asn Asn Ser Glu Gly Ala Asp Ala Gln Thr Gly Asn Lys
 65                  70                  75                  80
Thr Arg Leu Ala Phe Ala Gly Leu Lys Tyr Ala Asp Val Gly Ser Phe
                 85                  90                  95
Asp Tyr Gly Arg Asn Tyr Gly Val Val Tyr Asp Ala Leu Gly Tyr Thr
                100                 105                 110
Asp Met Leu Pro Glu Phe Gly Asp Thr Ala Tyr Ser Asp Asp Phe
                115                 120                 125
Phe Val Gly Arg Val Gly Val Ala Thr Tyr Arg Asn Ser Asn Phe
130                 135                 140
Phe Gly Leu Val Asp Gly Leu Asn Phe Ala Val Gln Tyr Leu Gly Lys
145                 150                 155                 160
Asn Glu Arg Asp Thr Ala Arg Arg Ser Asn Gly Asp Gly Val Gly Gly
                165                 170                 175
Ser Ile Ser Tyr Glu Tyr Glu Gly Phe Gly Ile Val Gly Ala Tyr Gly
                180                 185                 190
Ala Ala Asp Arg Thr Asn Leu Gln Glu Ala Gln Pro Leu Gly Asn Gly
                195                 200                 205
Lys Lys Ala Glu Gln Trp Ala Thr Gly Leu Lys Tyr Asp Ala Asn Asn
                210                 215                 220
Ile Tyr Leu Ala Ala Asn Tyr Gly Glu Thr Arg Asn Ala Thr Pro Ile
225                 230                 235                 240
Thr Asn Lys Phe Thr Asn Thr Ser Gly Phe Ala Asn Lys Thr Gln Asp
                245                 250                 255
Val Leu Leu Val Ala Gln Tyr Gln Phe Asp Phe Gly Leu Arg Pro Ser
                260                 265                 270
Ile Ala Tyr Thr Lys Ser Lys Ala Lys Asp Val Glu Gly Ile Gly Asp
                275                 280                 285
Val Asp Leu Val Asn Tyr Phe Glu Val Gly Ala Thr Tyr Tyr Phe Asn
                290                 295                 300
Lys Asn Met Ser Thr Tyr Val Asp Tyr Ile Ile Asn Gln Ile Asp Ser
305                 310                 315                 320
Asp Asn Lys Leu Gly Val Gly Ser Asp Asp Thr Val Ala Val Gly Ile
                325                 330                 335
Val Tyr Gln Phe Ala
                340

<210> SEQ ID NO 10
<211> LENGTH: 225
<212> TYPE: DNA
<213> ORGANISM: Nephila clavipes

<400> SEQUENCE: 10
atgagaggat cgcatcacca tcaccatcac ggatccatgg ctagcggtga cctgaaaaac     60
aaagtggccc agctgaaaag gaaagttaga tctctgaaag ataaagcggc tgaactgaaa    120
caagaagtct cgagactgga aaatgaaatc gaagacctga agccaaaat tggtgacctg     180 aataacacta gtgggatccg tcgacctgca gccaagctta attag                    225

<210> SEQ ID NO 11
<211> LENGTH: 74
<212> TYPE: PRT
<213> ORGANISM: Nephila clavipes

<400> SEQUENCE: 11
```

```
Met Arg Gly Ser His His His His His Gly Ser Met Ala Ser Gly
 1               5                  10              15

Asp Leu Lys Asn Lys Val Ala Gln Leu Lys Arg Lys Val Arg Ser Leu
                20              25              30

Lys Asp Lys Ala Ala Glu Leu Lys Gln Glu Val Ser Arg Leu Glu Asn
            35              40              45

Glu Ile Glu Asp Leu Lys Ala Lys Ile Gly Asp Leu Asn Asn Thr Ser
        50              55              60

Gly Ile Arg Arg Pro Ala Ala Lys Leu Asn
 65              70
```